(12) United States Patent
Cartier et al.

(10) Patent No.: US 11,464,537 B2
(45) Date of Patent: Oct. 11, 2022

(54) DEVICE AND METHOD FOR REMOVING MATERIAL FROM A HOLLOW ANATOMICAL STRUCTURE

(71) Applicant: AngioDynamics, Inc., Latham, NY (US)

(72) Inventors: William A Cartier, Glenville, NY (US); William C Hamilton, Jr., Queensbury, NY (US); James J Mitchell, Ballston Spa, NY (US); Daniel T Lagoe, St. Louis, MO (US)

(73) Assignee: AngioDynamics, Inc., Latham, NY (US)

( * ) Notice: Subject to any disclaimer, the term of this patent is extended or adjusted under 35 U.S.C. 154(b) by 294 days.

(21) Appl. No.: 16/797,188

(22) Filed: Feb. 21, 2020

(65) Prior Publication Data
US 2020/0187976 A1    Jun. 18, 2020

Related U.S. Application Data

(63) Continuation of application No. 14/708,355, filed on May 11, 2015, now Pat. No. 10,568,654, which is a
(Continued)

(51) Int. Cl.
*A61B 17/3207* (2006.01)
*A61B 17/221* (2006.01)
(Continued)

(52) U.S. Cl.
CPC .... *A61B 17/320725* (2013.01); *A61B 17/221* (2013.01); *A61B 17/320758* (2013.01);
(Continued)

(58) Field of Classification Search
CPC .......... A61B 17/221; A61B 17/320725; A61B 17/320758; A61B 2017/00685;
(Continued)

(56) References Cited

U.S. PATENT DOCUMENTS

| | | |
|---|---|---|
| 3,831,587 A | 8/1974 | Boyd |
| 4,046,150 A | 9/1977 | Schwartz |

(Continued)

FOREIGN PATENT DOCUMENTS

| | | |
|---|---|---|
| WO | 2005079678 A1 | 9/2005 |
| WO | 2011144336 | 11/2011 |

OTHER PUBLICATIONS

Nael et al., Endovascular Management of Central Thoracic Veno-Occlusive Diseases in Hemodialysis Patients: A Single Institutional Experience in 69 Consecutive Patients, Journal of Vascular Interventional Radiology, vol. 20, No. 1, 2009, pp. 46-51.

(Continued)

*Primary Examiner* — Jocelin C Tanner
(74) *Attorney, Agent, or Firm* — DLA Piper LLP (US)

(57) ABSTRACT

A medical device for removing a material from a hollow anatomical structure is provided. The device may include a shaft member. The device may include an expandable centering element near the distal end of the device. The device may include a macerator element either attached to the shaft or independent and freely moveable from the shaft. Alternatively, the device may include a rotating wire attached to the macerator element. The device may include an aspiration lumen in for removal of material. The device may include a drive shaft attached to a motor and used to rotate the macerator element. The device may be used in combination with a distal occlusion element, which may be either a radially expandable filter or balloon member.

20 Claims, 23 Drawing Sheets

Related U.S. Application Data continuation of application No. 13/420,913, filed on Mar. 15, 2012, now Pat. No. 9,055,964.

(60) Provisional application No. 61/585,348, filed on Jan. 11, 2012, provisional application No. 61/521,494, filed on Aug. 9, 2011, provisional application No. 61/452,838, filed on Mar. 15, 2011.

(51) Int. Cl.
  *A61B 17/22* (2006.01)
  *A61B 90/00* (2016.01)

(52) U.S. Cl.
  CPC .............. *A61B 2017/2212* (2013.01); *A61B 2017/2215* (2013.01); *A61B 2017/22038* (2013.01); *A61B 2017/22067* (2013.01); *A61B 2017/22068* (2013.01); *A61B 2017/320716* (2013.01); *A61B 2017/320733* (2013.01); *A61B 2017/320775* (2013.01); *A61B 2090/08021* (2016.02); *A61B 2217/005* (2013.01)

(58) Field of Classification Search
  CPC ........... A61B 2017/22038; A61B 2017/22067; A61B 2017/22068; A61B 2017/2212; A61B 2017/2215; A61B 2017/320716; A61B 2017/320733; A61B 2017/320775; A61B 2090/08021; A61B 2217/005
  See application file for complete search history.

(56) References Cited

U.S. PATENT DOCUMENTS

| | | |
|---|---|---|
| 4,273,128 A | 6/1981 | Lary |
| 4,437,856 A | 3/1984 | Valli |
| 4,445,509 A | 5/1984 | Auth |
| 4,469,100 A | 9/1984 | Hardwick |
| 4,646,736 A | 3/1987 | Auth |
| 4,664,112 A | 5/1987 | Kensey |
| 4,671,796 A | 6/1987 | Groshong |
| 4,681,564 A | 7/1987 | Landreneau |
| 4,693,243 A | 9/1987 | Buras |
| 4,696,667 A | 9/1987 | Masch |
| 4,729,763 A | 3/1988 | Henrie |
| 4,747,821 A | 5/1988 | Kensey |
| 4,749,376 A | 6/1988 | Kensey |
| 4,790,812 A | 12/1988 | Hawkins, Jr. |
| 4,857,045 A | 8/1989 | Rydell |
| 4,857,046 A | 8/1989 | Stevens |
| 4,886,061 A | 12/1989 | Fischell |
| 4,895,166 A | 1/1990 | Farr |
| 4,895,560 A | 1/1990 | Papantonakos |
| 4,921,478 A | 5/1990 | Solano |
| 4,990,134 A | 2/1991 | Auth |
| 4,990,151 A | 2/1991 | Wallsten |
| 5,011,488 A | 4/1991 | Ginsburg |
| 5,019,089 A | 5/1991 | Farr |
| 5,030,201 A | 7/1991 | Palestrant |
| 5,074,841 A | 12/1991 | Ademovic |
| 5,084,052 A | 1/1992 | Jacobs |
| 5,092,877 A | 3/1992 | Pinchuk |
| 5,098,440 A | 3/1992 | Hillstead |
| 5,100,423 A | 3/1992 | Fearnot |
| 5,114,399 A | 5/1992 | Kovalcheck |
| 5,158,564 A | 10/1992 | Schnepp-Pesch |
| 5,211,651 A | 5/1993 | Reger |
| 5,226,909 A | 7/1993 | Evans |
| 5,257,974 A | 11/1993 | Cox |
| 5,273,526 A | 12/1993 | Dance |
| 5,306,250 A | 4/1994 | March |
| 5,334,208 A | 8/1994 | Soehendra |
| 5,423,799 A | 6/1995 | Shiu |
| 5,464,408 A | 11/1995 | Duc |
| 5,474,563 A | 12/1995 | Myler |
| 5,490,859 A | 2/1996 | Mische |
| 5,520,697 A | 5/1996 | Lindenberg |
| 5,540,707 A | 7/1996 | Ressemann |
| 5,569,275 A | 10/1996 | Kotula |
| 5,571,086 A | 11/1996 | Kaplan |
| 5,628,746 A | 5/1997 | Clayman |
| 5,632,755 A | 5/1997 | Nordgren |
| 5,643,309 A | 7/1997 | Myler |
| 5,653,684 A | 8/1997 | Laptewicz |
| 5,733,302 A | 3/1998 | Myler |
| 5,772,629 A | 6/1998 | Kaplan |
| 5,776,141 A | 7/1998 | Klein |
| 5,785,715 A | 7/1998 | Schatz |
| 5,843,103 A | 12/1998 | Wulfman |
| 5,868,753 A | 2/1999 | Schatz |
| 5,873,882 A | 2/1999 | Straub |
| 5,910,144 A | 6/1999 | Hayashi |
| 5,941,895 A | 8/1999 | Myler |
| 6,001,112 A | 12/1999 | Taylor |
| 6,106,531 A | 8/2000 | Schatz |
| 6,187,016 B1 | 2/2001 | Hedges |
| 6,203,537 B1 | 3/2001 | Adrian |
| 6,206,898 B1 | 3/2001 | Honeycutt |
| 6,241,738 B1 | 6/2001 | Dereume |
| 6,280,413 B1 | 8/2001 | Clark |
| 6,280,464 B1 | 8/2001 | Hayashi |
| 6,283,940 B1 | 9/2001 | Mulholland |
| 6,394,978 B1 | 5/2002 | Boyle |
| 6,443,966 B1 | 9/2002 | Shiu |
| 6,451,036 B1 | 9/2002 | Heitzmann |
| 6,454,775 B1 | 9/2002 | Demarais |
| 6,454,779 B1 | 9/2002 | Taylor |
| 6,508,782 B1 | 1/2003 | Evans |
| 6,547,754 B1 | 4/2003 | Evans |
| 6,569,181 B1 | 5/2003 | Burns |
| 6,582,396 B1 | 6/2003 | Parodi |
| 6,602,264 B1 | 8/2003 | McGuckin, Jr. |
| 6,660,014 B2 | 12/2003 | Demarais |
| 6,666,874 B2 | 12/2003 | Heitzmann |
| 6,676,692 B2 | 1/2004 | Rabkin |
| 6,679,893 B1 | 1/2004 | Tran |
| 6,702,830 B1 | 3/2004 | Demarais |
| 6,719,717 B1 | 4/2004 | Johnson |
| 6,749,619 B2 | 6/2004 | Ouriel |
| 6,802,846 B2 | 10/2004 | Hauschild |
| 6,837,901 B2 | 1/2005 | Rabkin |
| 6,945,977 B2 | 9/2005 | Demarais |
| 7,014,913 B2 | 3/2006 | Pacetti |
| 7,108,704 B2 | 9/2006 | Trerotola |
| 7,153,320 B2 | 12/2006 | Euteneuer |
| 7,172,610 B2 | 2/2007 | Heitzmann |
| 7,235,088 B2 | 6/2007 | Pintor |
| 7,258,696 B2 | 8/2007 | Rabkin |
| 7,351,255 B2 | 4/2008 | Andreas |
| 7,479,147 B2 | 1/2009 | Honeycutt |
| 7,655,016 B2 | 2/2010 | Demarais |
| 7,771,445 B2 | 8/2010 | Heitzmann |
| 7,842,010 B2 | 11/2010 | Bonnette |
| 7,842,055 B2 | 11/2010 | Pintor |
| 7,862,575 B2 | 1/2011 | Tal |
| 7,879,022 B2 | 2/2011 | Bonnette |
| 7,892,273 B2 | 2/2011 | George |
| 7,912,531 B1 | 3/2011 | Chiu |
| 8,034,095 B2 | 10/2011 | Randolph |
| 8,038,704 B2 | 10/2011 | Sherburne |
| 8,075,510 B2 | 12/2011 | Aklog |
| 8,167,903 B2 | 5/2012 | Hardert |
| 8,317,859 B2 | 11/2012 | Snow |
| 8,470,016 B2 | 6/2013 | Sherburne |
| 8,734,374 B2 | 5/2014 | Aklog |
| 8,828,073 B2 | 9/2014 | Sherburne |
| 8,945,141 B2 | 2/2015 | Cahill |
| 9,351,861 B2 | 5/2016 | Sherburne |
| 2001/0011179 A1 | 8/2001 | Adams |
| 2002/0010487 A1 | 1/2002 | Evans |
| 2002/0072764 A1 | 6/2002 | Sepetka |
| 2002/0120277 A1 | 8/2002 | Hauschild |
| 2002/0143387 A1 | 10/2002 | Soetikno |

(56) References Cited

U.S. PATENT DOCUMENTS

| | | |
|---|---|---|
| 2002/0151918 A1* | 10/2002 | Lafontaine ..... A61B 17/320758 |
| | | 606/159 |
| 2002/0161377 A1 | 10/2002 | Rabkin |
| 2002/0161427 A1 | 10/2002 | Rabkin |
| 2002/0188276 A1 | 12/2002 | Evans |
| 2003/0023204 A1 | 1/2003 | Vo |
| 2003/0055445 A1 | 3/2003 | Evans |
| 2003/0195537 A1 | 10/2003 | Dubrul |
| 2003/0199890 A1 | 10/2003 | Dubrul |
| 2003/0236533 A1 | 12/2003 | Wilson |
| 2004/0082962 A1 | 4/2004 | Demarais |
| 2004/0147939 A1 | 7/2004 | Rabkin |
| 2004/0181237 A1 | 9/2004 | Forde |
| 2004/0210298 A1 | 10/2004 | Rabkin |
| 2005/0004594 A1 | 1/2005 | Nool |
| 2005/0080431 A1 | 4/2005 | Levine |
| 2005/0080480 A1 | 4/2005 | Bolea |
| 2006/0095015 A1 | 5/2006 | Hobbs |
| 2006/0129095 A1 | 6/2006 | Pinchuk |
| 2006/0189930 A1 | 8/2006 | Lary |
| 2006/0195138 A1 | 8/2006 | Goll |
| 2006/0200191 A1 | 9/2006 | Zadno-Azizi |
| 2006/0253145 A1* | 11/2006 | Lucas .............. A61B 17/32075 |
| | | 606/159 |
| 2007/0027520 A1 | 2/2007 | Sherburne |
| 2007/0118072 A1 | 5/2007 | Nash |
| 2007/0239182 A1 | 10/2007 | Glines |
| 2008/0033482 A1 | 2/2008 | Kusleika |
| 2008/0249558 A1 | 10/2008 | Cahill |
| 2009/0018567 A1 | 1/2009 | Escudero |
| 2009/0099581 A1 | 4/2009 | Kim |
| 2009/0222035 A1 | 9/2009 | Schneiderman |
| 2009/0292307 A1 | 11/2009 | Razack |
| 2009/0306702 A1 | 12/2009 | Miloslavski |
| 2010/0057184 A1 | 3/2010 | Randolph |
| 2011/0190806 A1 | 8/2011 | Wittens |
| 2012/0016455 A1 | 1/2012 | Sherburne |
| 2012/0059309 A1 | 3/2012 | Di Palma |
| 2012/0059356 A1 | 3/2012 | Di Palma |
| 2012/0197277 A1* | 8/2012 | Stinis ............. A61B 17/320758 |
| | | 606/190 |
| 2012/0253358 A1* | 10/2012 | Golan .................. A61B 17/221 |
| | | 606/128 |
| 2013/0289694 A1 | 10/2013 | Sherburne |
| 2014/0350591 A1 | 11/2014 | Sherburne |
| 2015/0127044 A1 | 5/2015 | Cahill |
| 2017/0333076 A1 | 11/2017 | Bruzzi |

OTHER PUBLICATIONS

Valji, et al., Pulsed-Spray Thrombolysis of Arterial and Bypass Graft Occlusion, American Roentgen Ray Society, pp. 617-621 (Mar. 1991).

International Search Report PCT-NL-08-050399 ISR dated Feb. 13, 2009, 3 pages.

Office Action dated Mar. 8, 2021 for U.S. Appl. No. 16/454,644 (pp. 1-9).

* cited by examiner

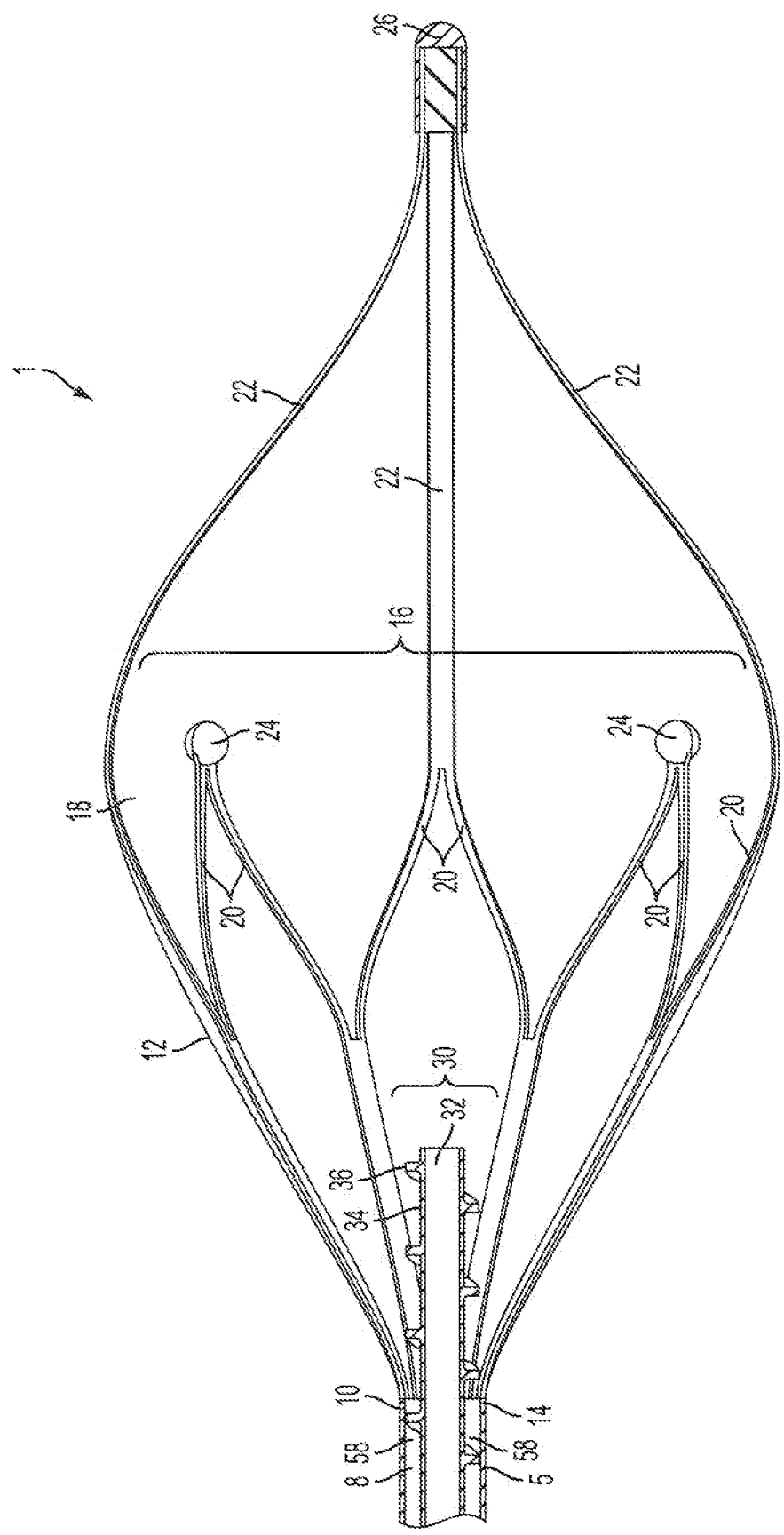

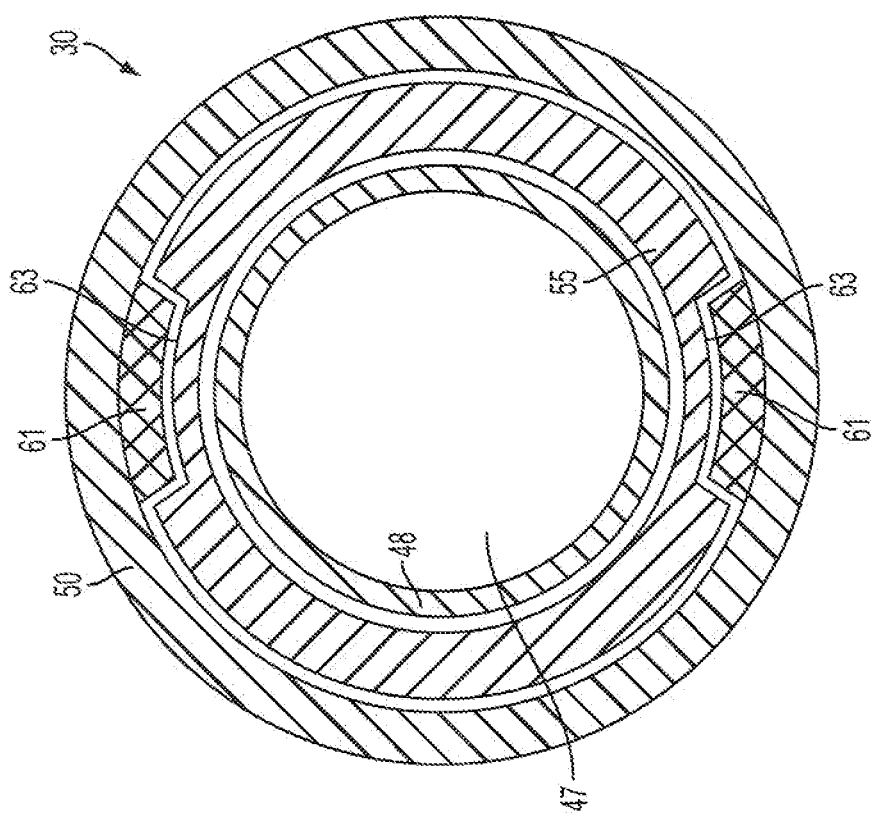

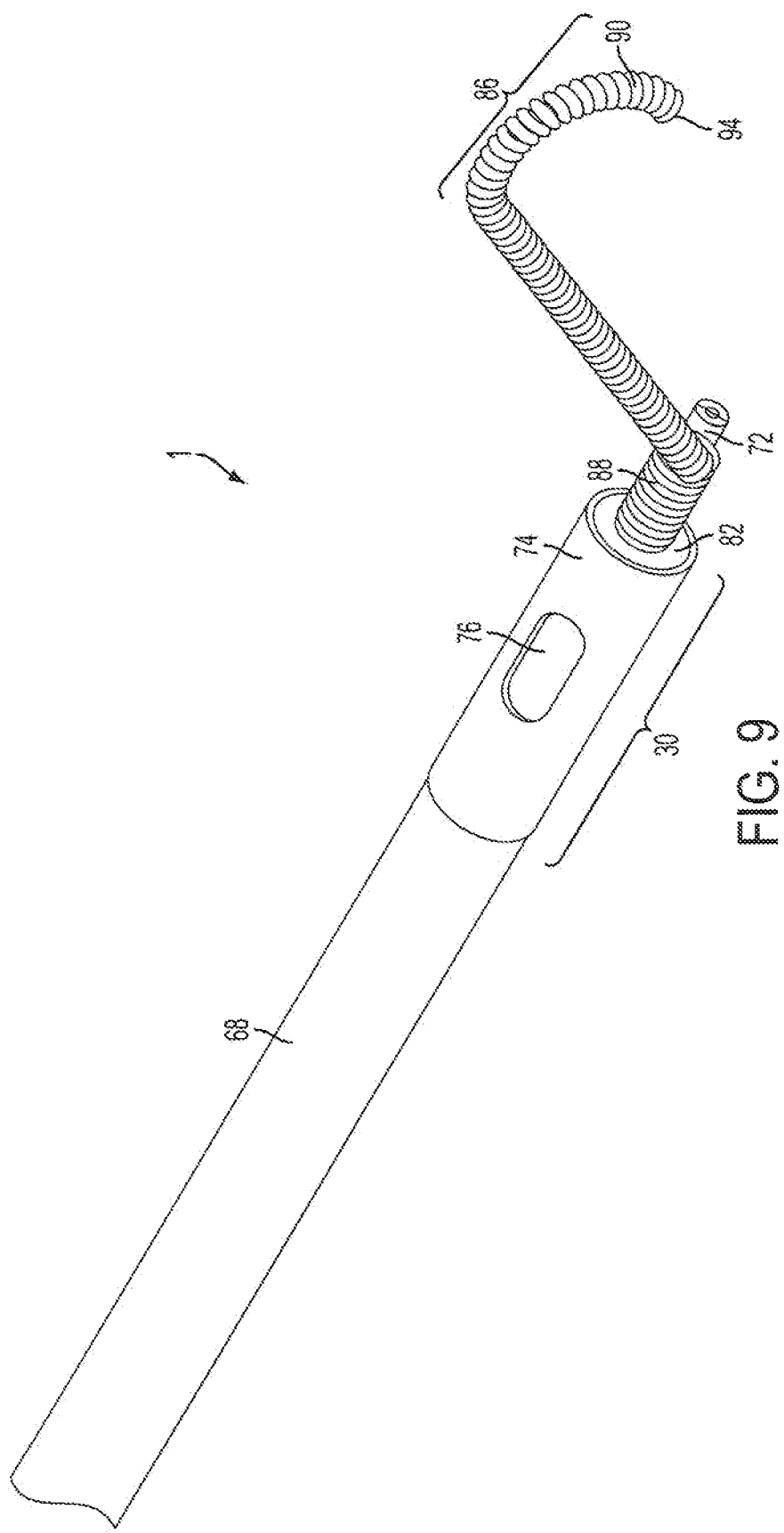

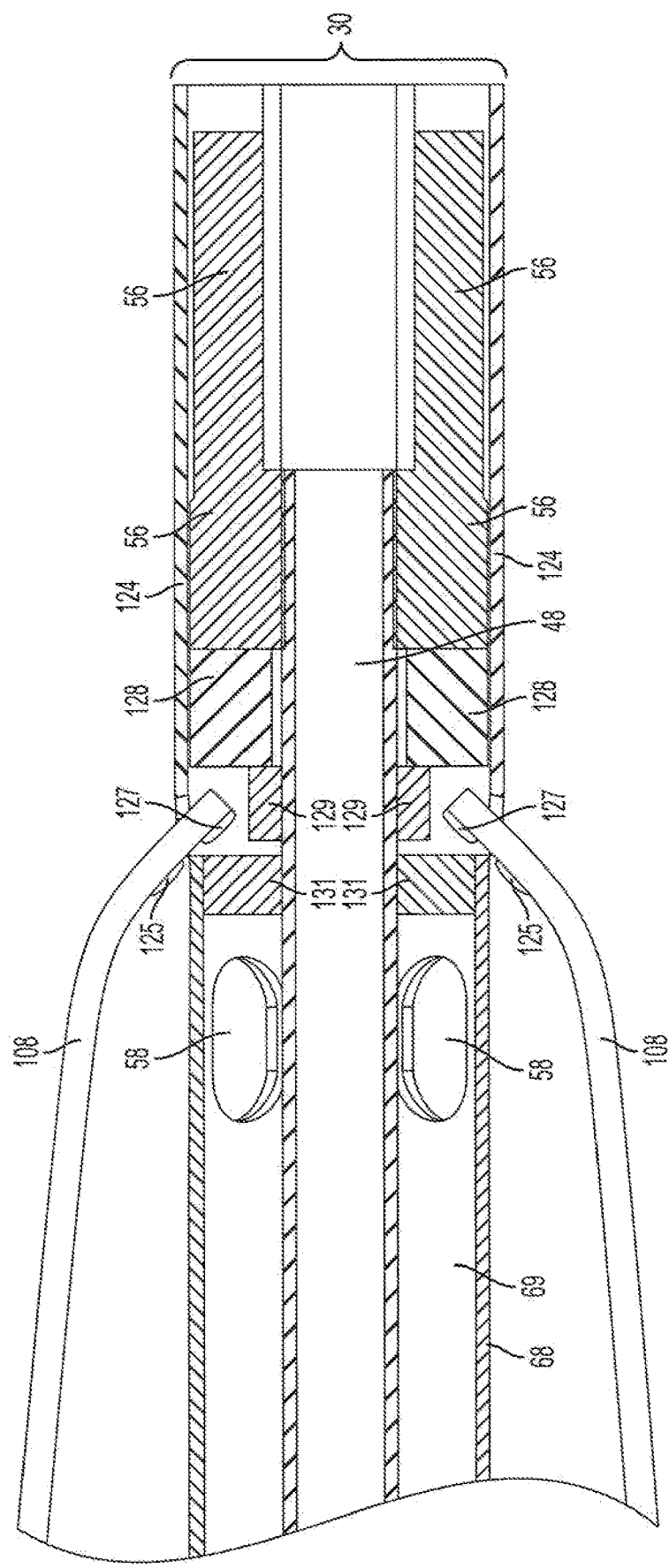

DEVICE AND METHOD FOR REMOVING MATERIAL FROM A HOLLOW ANATOMICAL STRUCTURE

CROSS REFERENCE TO RELATED APPLICATIONS

This application is a continuation of U.S. patent application Ser. No. 14/708,355, filed May 11, 2015, now U.S. Pat. No. 10,568,654, which is a continuation of U.S. patent application Ser. No. 13/420,913, filed Mar. 15, 2012, now U.S. Pat. No. 9,055,964, which claims priority under 35 U.S.C. 119(e) to U.S. Provisional Application No. 61/452,838, filed Mar. 15, 2011, U.S. Provisional Application No. 61/521,494, filed Aug. 9, 2011, and U.S. Provisional Application No. 61/585,348, filed Jan. 1, 2012, all of which are incorporated herein by reference.

BACKGROUND

Common types of treatment for removal of thrombus include fluid delivery, such as a lytic or other blood thinning medication. For example, a doctor may deliver a desired drug, such as lytic, to the treatment site adjacent to the clot in order to break down the clot matter. This manner of treatment may result in small pieces of clot remaining in the vessel after treatment, commonly attached to the vessel wall. Problems with known methods of clot removal is it's a common requirement for the patient to remain overnight in the hospital or the treatment may not completely remove the clot from the vessel. An object of this invention is to provide a mechanical means for aiding in the complete removal of clot material.

FIELD OF THE INVENTION

The present invention relates generally to devices for removing material from a hollow anatomical structure. More specifically, the invention relates to mechanically treating the targeted area with an elongated device having an expandable or inverted centering element, a drive shaft attached to a rotatable macerator element for breaking up, dislodging, or dissolving clot material, and an aspiration or vacuum source for removal of clot material. Additionally, the device contains open fluid communication channels and is capable of delivering various fluids, drugs or other medical preparations to a treatment site within a lumen of a blood vessel or another cavity or lumen within a patient's body.

SUMMARY OF THE DISCLOSURE

According to the principles of the present invention, a medical device for removing material from a hollow anatomical structure is provided. The device may include a hollow shaft member having a proximal and distal end and a drive shaft coaxially disposed within hollow shaft member. The drive shaft has a proximal and distal end and the proximal end may be attached to a motor or other drive mechanism. The device may also include an expandable or inverted centering element disposed near the distal end of the elongated shaft. The expandable or inverted segment may expand to a predetermined shape automatically upon deployment from a sheath, or alternatively the expandable or inverted segment may be hinged to the distal end of the shaft for manual expansion.

The device includes a macerator element near the distal end of the hollow shaft. The macerator element may be attached to the distal end of the drive shaft. The macerator element may be comprised of an auger element, rotating element, shearing member coaxially disposed and freely rotatable within an outer tubular extension, a rotating wire, or any combination of these various elements. The macerator element rotates along the central axis of the device to aid in mechanically removing, dissolving, disrupting, liquefying, or breaking down clot material from within a hollow anatomical structure. The rotations per minute and means for removing the clot material may change depending on the embodiment of macerator element being used. The device may include an aspiration or vacuum element to aid in removal of clot material. The device may be used in combination with a distal protection element, such as an expandable filter or inflatable balloon member.

A method for removing material from a hollow anatomical structure is provided, which includes the following steps. If used, the distal protection element may be placed at the treatment site. The device described above may be inserted near the treatment site by either back-loading it over a pre-placed guidewire or by inserting the device through a pre-placed procedure sheath. The expandable or inverted segment may expand to a predetermined shape automatically upon deployment from a sheath, or alternatively the expandable or inverted segment may be manual expanded and deployed. Once the device is properly in place, the drive shaft is attached to the motor mechanism which is then activated. As the drive shaft is rotated this also rotates the maceration element once macerator element has been activated the aspiration mechanism is then activated. Procedure is performed as the macerator element removes, dissolves, disrupts, liquefies, or breaks down clot material from within a hollow anatomical structure and this material is removed through the aspiration area. Optionally, the user may elect to deliver fluid through the device at any time throughout the procedure. Once procedure is complete the device is removed.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, wherein:

FIG. 1B illustrates a partial plan side view of the distal portion of the device showing the expandable centering element and auger element.

FIG. 4C illustrates a cross-sectional view of the device taken along lines B-B of FIG. 5.

FIG. 9 is a partial, isometric view of a macerator assembly with a shearing macerator element and a rotating wire element for macerating the clot mass.

FIG. 11C illustrates an enlarged, cross-sectional view of the manually expandable cage section in an undeployed position.

DETAILED DESCRIPTION OF THE INVENTION

Figure 1A:
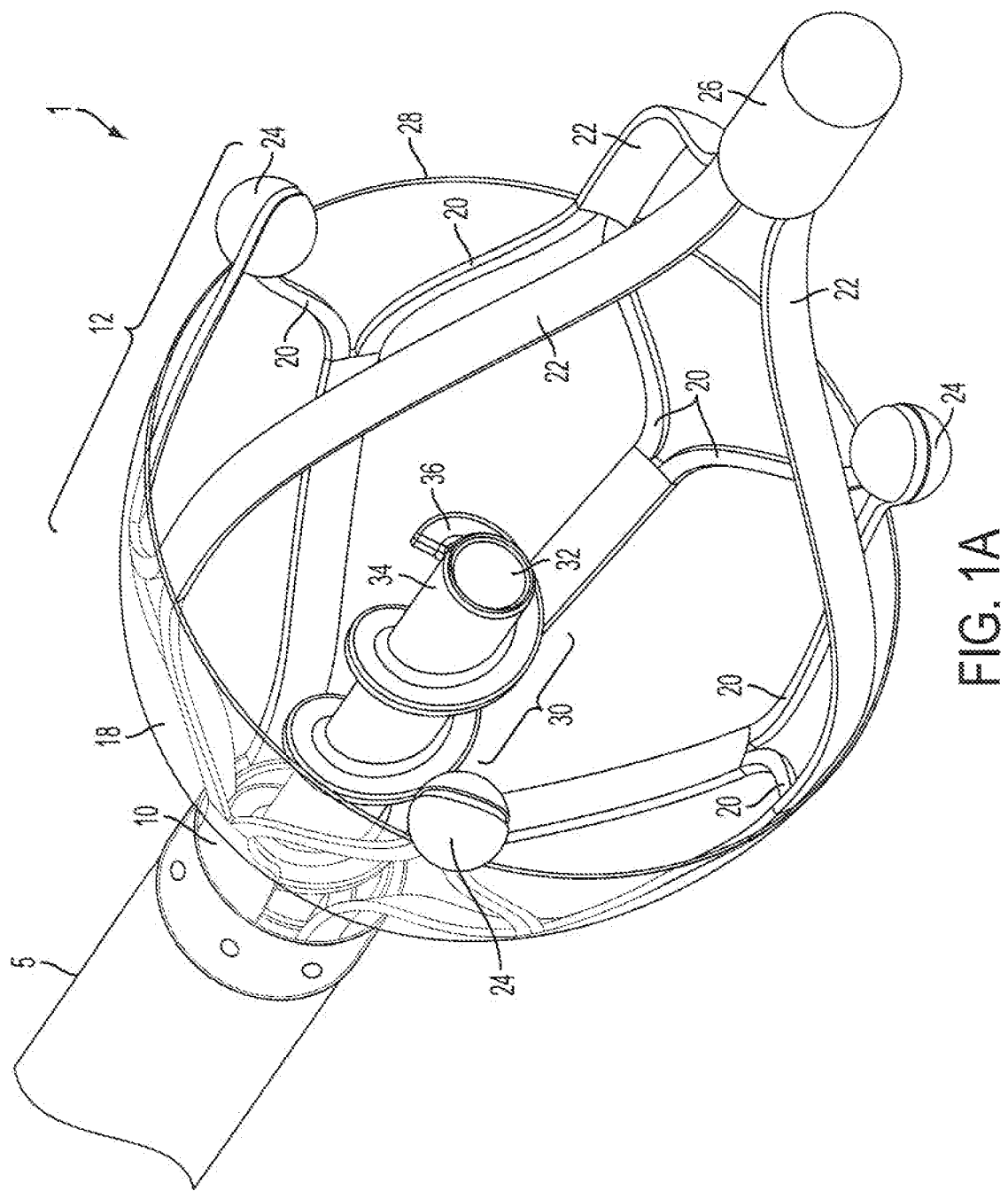
FIG. 1A depicts an isometric partial view of the distal portion of the device showing the expandable centering element and auger element.

The present invention can be understood more readily by reference to the following detailed description and the examples included therein and to the figures and their previous and following description. The drawings, which are not necessarily to scale, depict selected preferred embodiments and are not intended to limit the scope of the invention. The detailed description illustrates by way of example, not by way of limitation, the principles of the invention.

The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting.

As used herein, the term "proximal" denotes the direction closer to the operator and the term "distal" denotes the direction closer to (inserted into) the patient.

The clot removal device of the present invention allows a user to mechanically dislodge, disrupt, dissolve, liquefy, break-down or remove a clot, thrombus or other build-up of material formed against a vessel wall. This invention is advantageous for treatment of build-up of material formed against a vessel wall because the material will be mechanically detached and removed away from the vessel wall which reduces reformation of localized clot post treatment. The treatment device may allow the user to manually control various aspects of the clot removal, including but not limited to the expansion and collapse of an expandable centering device, cage, filter or inverted centering element, the speed or rotation of the macerator element, and the aspiration of dislodged and broken down clot material for complete removal from the vessel. Additionally, the invention allows for the option of delivery of fluid to the treatment site.

Referring now in detail to the drawings, in which like reference numerals indicate like parts or elements throughout the several views, in various embodiments, presented herein is a treatment device intended for the removal of clot material from a vessel.

FIGS. 1A-2B illustrate one aspect of the invention wherein thrombus may be removed from a vessel using clot removal device 1. The clot removal device 1 may be comprised of an elongate outer shaft 5, a macerator element 30, expandable member 12, and aspiration area 58. The outer shaft 5 has a through lumen 8, as shown in FIG. 1B, which extends from a proximal end of the device (not shown) to a proximal end 10 of an expandable member 12 where the through lumen 8 terminates in a distal end 14. Clot removal device 1 may be in the range of 6 F to 20 F in size so as to facilitate removal of clot from both small and large vessels. A preferred size of the clot removal device 1 may be 8 F wherein the outer shaft 5 may have an outer diameter of 0.103 inches and an inner diameter of 0.086 inches.

An advantage of the expandable member 12 is that it may be compressed during insertion of the device 1, and once device 1 is placed at treatment site expandable member 12 may expand out radially to center the macerator element 30 within center of vessel lumen. Expandable member 12 may be comprised of a frame 16. When expanded, frame 16 extends radially outward from the distal end 14 of shaft 5 to a maximum diameter before converging radially inward toward distal leading end 26. Frame 16 is comprised of proximal legs which split into wire members 20. Adjacent wire members 20 extend distally and converge either at an atraumatic bead 24 or to form a plurality of distal frame legs 22. The wire members 20 may be made from a shape memory material, such as nitinol or stainless steel, so that the expandable member 12 may be compressed or collapsed during insertion and then fully expanded to a preset shape once at the target site. Alternatively, cover 18 may be positioned over the frame 16. The cover 18 may be either a permeable material or non-permeable material.

In the depicted embodiment the plurality of distal frame legs 22 may extend from the remaining alternate converging wire members 20 distally in an inward direction toward the longitudinal axis of the clot removal device 1. Distal frame legs 22 terminate in a distal leading end 26. Distal frame legs 22 may extend distally, approximately 0.5 inches to 2.0 inches, from a distal end 28 of the non-permeable material 18 to the distal leading end 26. Although the figures detail four distal frame legs 22, this may only be exemplary and any reasonable number of legs may be employed.

Distal leading end 26 and beads 24 may be used for atraumatic advancement of the clot removal device 1 through the vessel and for preventing perforation through the vessel wall. When expanded, the expandable member 12 centers the clot removal device 1 within the center of the target vessel. In its expanded position the expanded member 12 may have a diameter in the range of 10 mm to 20 mm. The user may advance the expandable member 12 towards the clot so distal frame legs 22 or beads 24 aid in mechanically agitating or disrupting the clot and assist in separating the clot mass from the vessel wall.

Clot removal device 1 further includes a macerator element 30. In this embodiment the macerator element 30 is comprised of an auger 32 element. Auger 32 consists of a longitudinal tube 34 body having a helical member 36 disposed along the outer surface of the tube 34. Auger 32 may be capable of clockwise and/or counter-clockwise movement. Longitudinal tube 34 may either consist of a solid or a hollow closed end tubular member. The auger 32 may be coaxially disposed within the through lumen 8 of the outer shaft 5 of the clot removal device 1. The auger 32 may extend approximately 0.25 inches to 5.0 inches from the distal end 14 of the outer shaft 5.

Figure 2A:
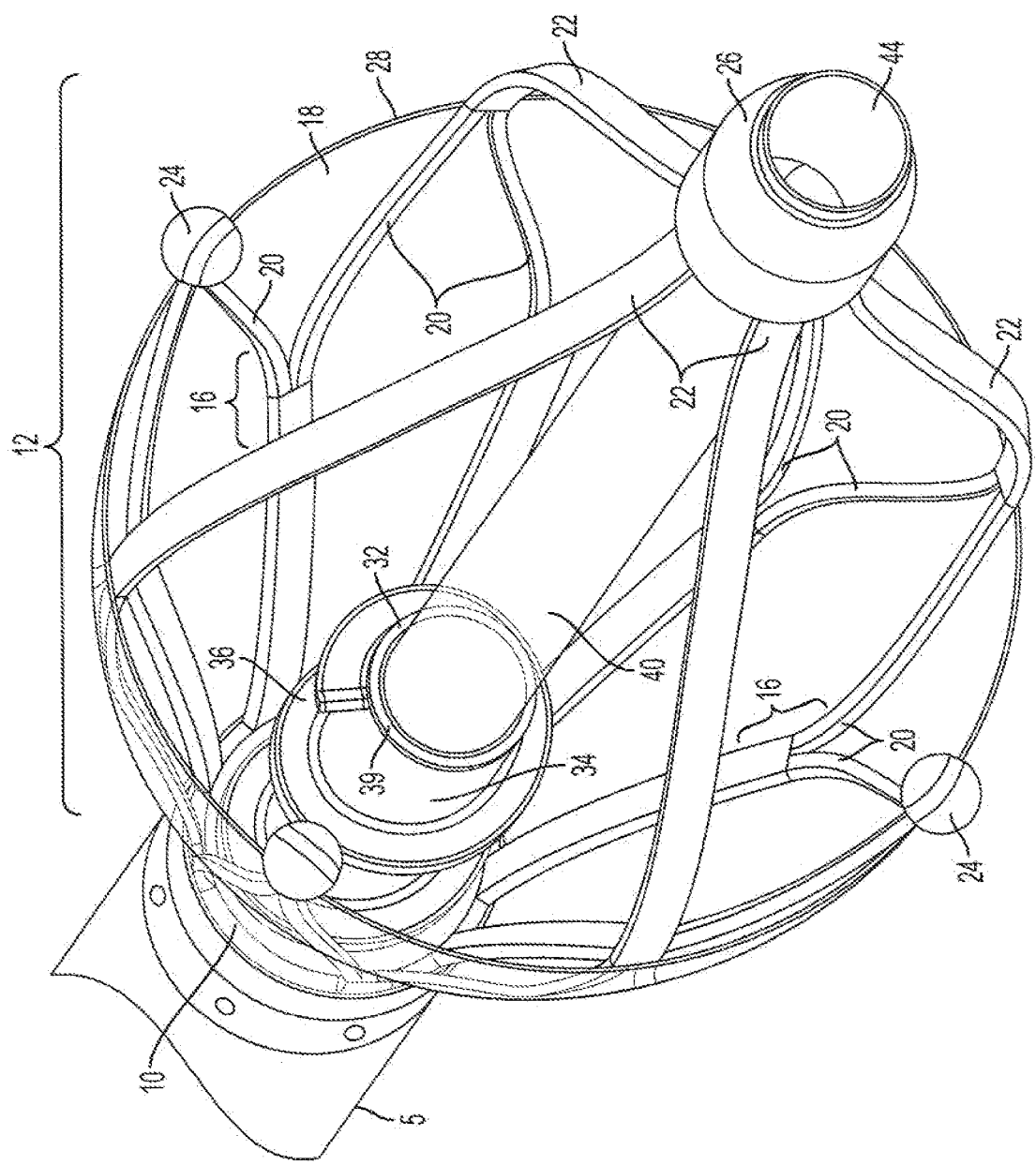
FIG. 2A depicts an isometric partial view of the distal portion of the device showing the expandable centering element and auger element with an inner shaft extending to the distal end of the centering element.
Figure 2B:
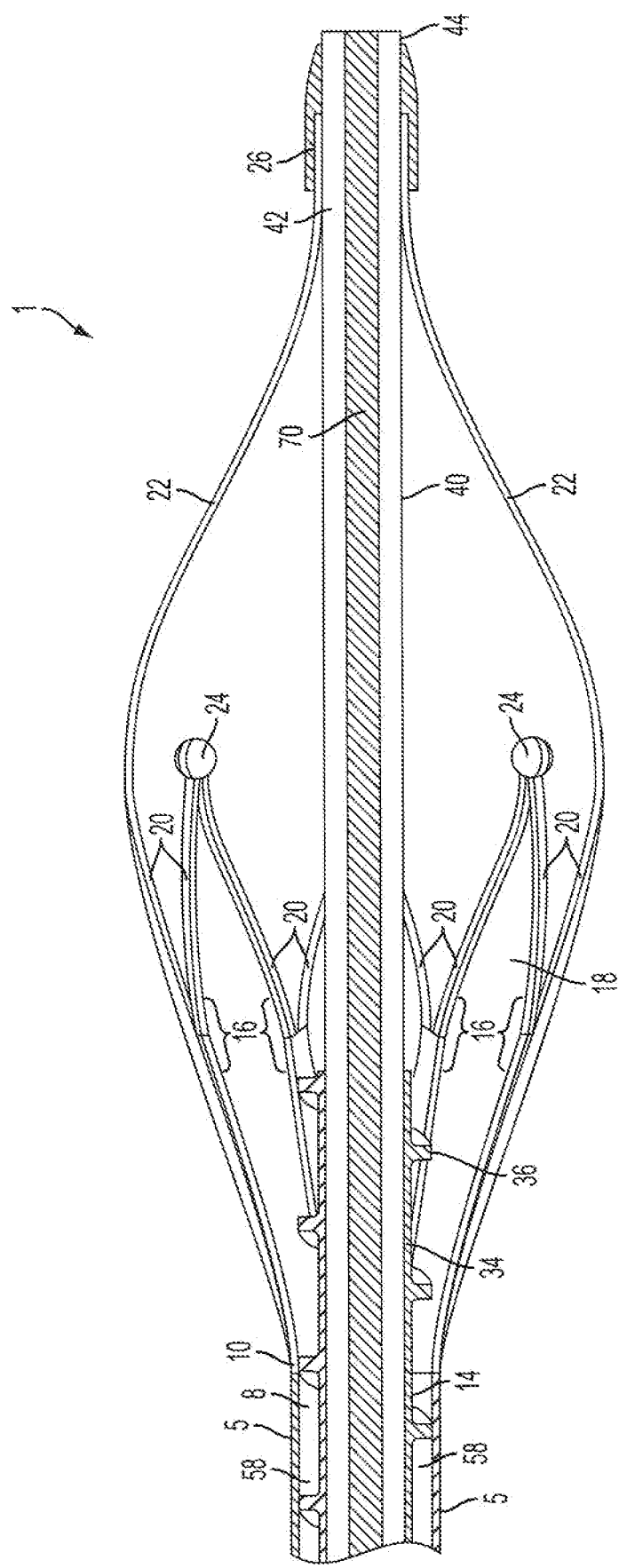
FIG. 2B illustrates a partial cross-sectional view of the distal portion of the device showing the expandable centering element and auger element with an inner shaft extending to the distal end of the centering element.

Alternatively, this embodiment may be used over a guidewire, as seen in FIG. 2A-2B. For example, coaxially positioned within lumen 38 of the auger 32 may be an inner shaft 40 which extends from the proximal end of the device and emerges from distal end 39 of the auger 32. Inner shaft 40 includes an inner through lumen 42 and further extends through the expandable member 12 to terminate at an open distal tip 44 to facilitate advancement of guidewire through the expandable cage portion of the device. The inner through lumen 42 of inner shaft 40 may provide for the introduction and removal of medical devices known in the art, such as guidewires, distal protection devices or occlusion balloons. As one example shown in FIG. 2B, a guidewire or distal occlusion element 70 may be advanced through the inner through lumen 42 and positioned distally of the target treatment area to capture any residual emboli created by the clot removal procedure. Alternatively, the device 1 may also be back-loaded over a guidewire that has already been placed at treatment site. Once the device 1 and distal occlusion element are in place, the auger 32 may then be activated and further advanced toward the clot to mechanically break down the clot material into smaller pieces. The user may aspirate the broken down clot material for removal through the aspiration area 58.

The auger 32 rotates around the central axis via connection to a drive shaft. The auger 32 may have the ability of being advanced and/or retracted within the through lumen 8 outer shaft 5 or may be stationary during use. The drive shaft may be secured to the inner lumen 38 of the auger 32 by conventional techniques such as, but not limited to, dog bone coupling, spline coupling, press fit, use of a known adhesive, or other known methods for coupling with ability to rotate. When activated, rotation of the drive shaft causes rotation of the auger 32 in either a clock-wise or counter-clockwise direction. During use the auger 32 may be rotated approximately up to 5,000 RPMs and may have a pitch in the range of 0.5 helical members per inch to 10 helical members per inch, with a preferred pitch of 8 helical members per inch. Although a pitch of 8 helical members per inch may be preferred, conceivably, the auger 32 may have helical members that vary in dimension per inch along the length of the auger 32.

Rotation of the auger 32 causes the clot mass to be drawn into an annular space 58 defined between the helical member 36 and the through lumen 8 outer shaft 5. As the clot mass is drawn into this annular space the clot may be sheared, chopped, or macerated into smaller fragments and may be aspirated. Clot removal device 1 may also be attached to an external vacuum syringe or pump (not shown) which provides the clot removal device 1 with the ability to aspirate small clot fragments from within the vessel and/or annular space of the clot removal device 1 for removal. The auger 32 and external vacuum syringe or pump may work together or independently to remove thrombus particles from the vessel and/or clot removal device 1.

For the method of this embodiment the clot removal device 1 may be introduced into the target vessel or other anatomical site using minimally invasive access techniques known in the art. During insertion, the expandable member 12 may be collapsed within a procedure sheath (not shown). The clot removal device 1 may be advanced into position adjacent the clot. The procedure sheath may be proximally retracted allowing for deployment of the expandable member 12. Distal leading end 26 of the legs 22 provides for atraumatic advancement or retraction of the clot removal device 1 through the vessel after expansion.

Expansion of the expandable member 12 centers the macerator element 30 of clot removal device 1 within the vessel. During expansion of the expandable member 12 the beads 24 aid in preventing perforation through the vessel wall. Upon proper positioning of the clot removal device 1 within the vessel the auger 32 may be advanced distally towards the thrombus or other material being removed from vessel (not shown). Activation of the driveshaft causes rotation and advancement of the auger 32 allowing helical member 36 to disrupt the clot by engaging and entangling materials within the clot, particularly fibrin fibers which make up a substantial portion of the clot material. Auger 32 may be advanced and/or retracted while rotating to disrupt the clot material. Clot material not aspirated through the movement of the auger 32 may be aspirated through aspiration area 58. The expandable member 12 may be rotated to assist in the dislodging or detaching of the clot from the vessel wall.

Although the current design anticipates disruption of the clot material without the use of a lysing agent, a practitioner might optionally use a lysing agent to further enhance treatment outcome during the procedure. The lysing agent may be introduced through the through lumen 8 of the outer shaft 8 or through the luminal space through the auger 32.

Upon completion of the procedure, if the auger 32 was advanced, the auger 32 may then be retracted to its original position and the clot removal device 1 may be withdrawn within the procedure sheath, thereby collapsing the expandable member 12 where any potentially remaining clot particles may be captured and removed as the clot removal device 1 may be withdrawn from the patient. This method contemplates clot disruption and removal with minimum risk of injury to the vessel.

Figure 3:
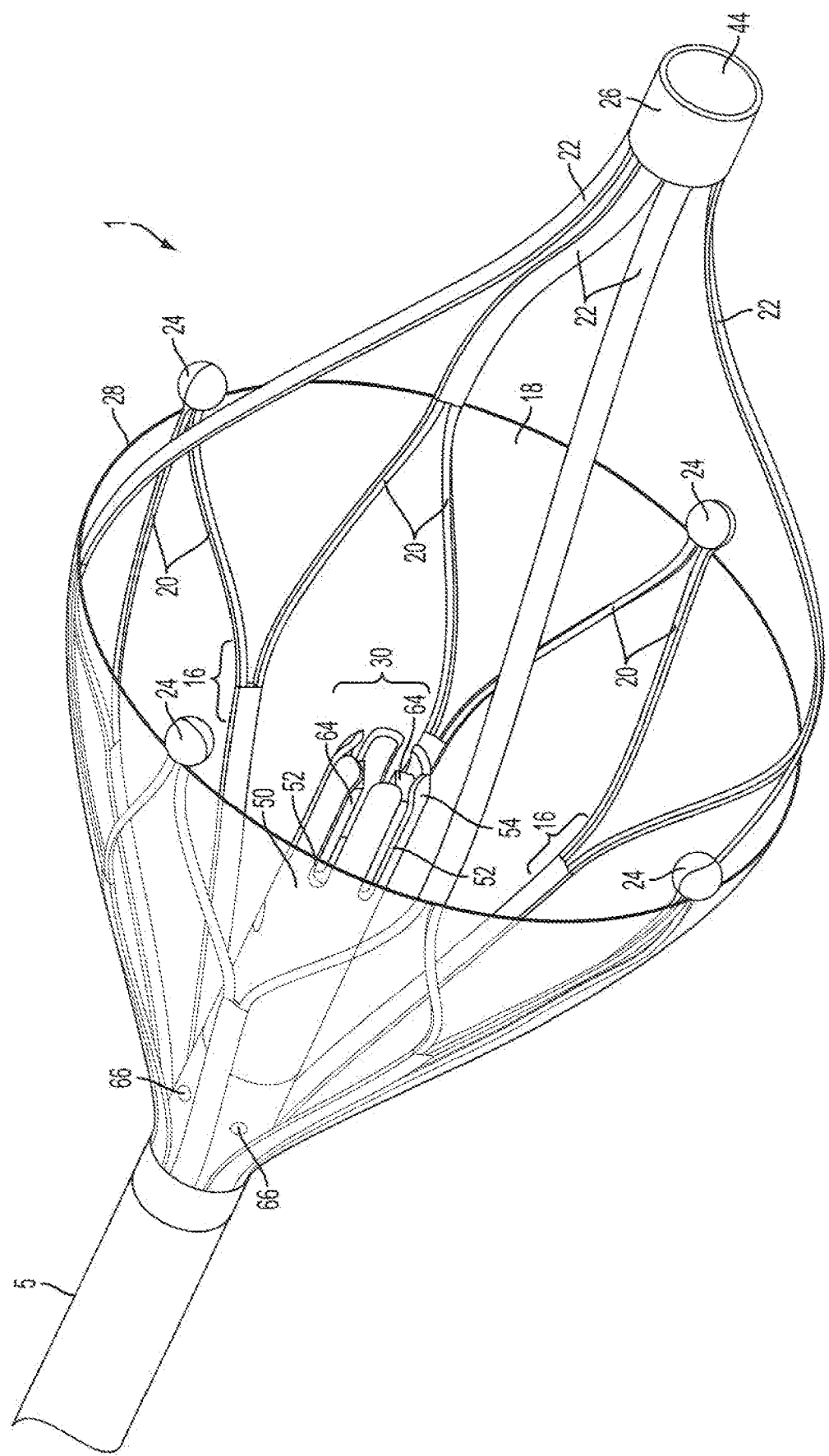
FIG. 3 is a partial, isometric view of the distal portion of the device illustrating another embodiment of the expandable centering element and rotating macerator element.
Figure 4A:
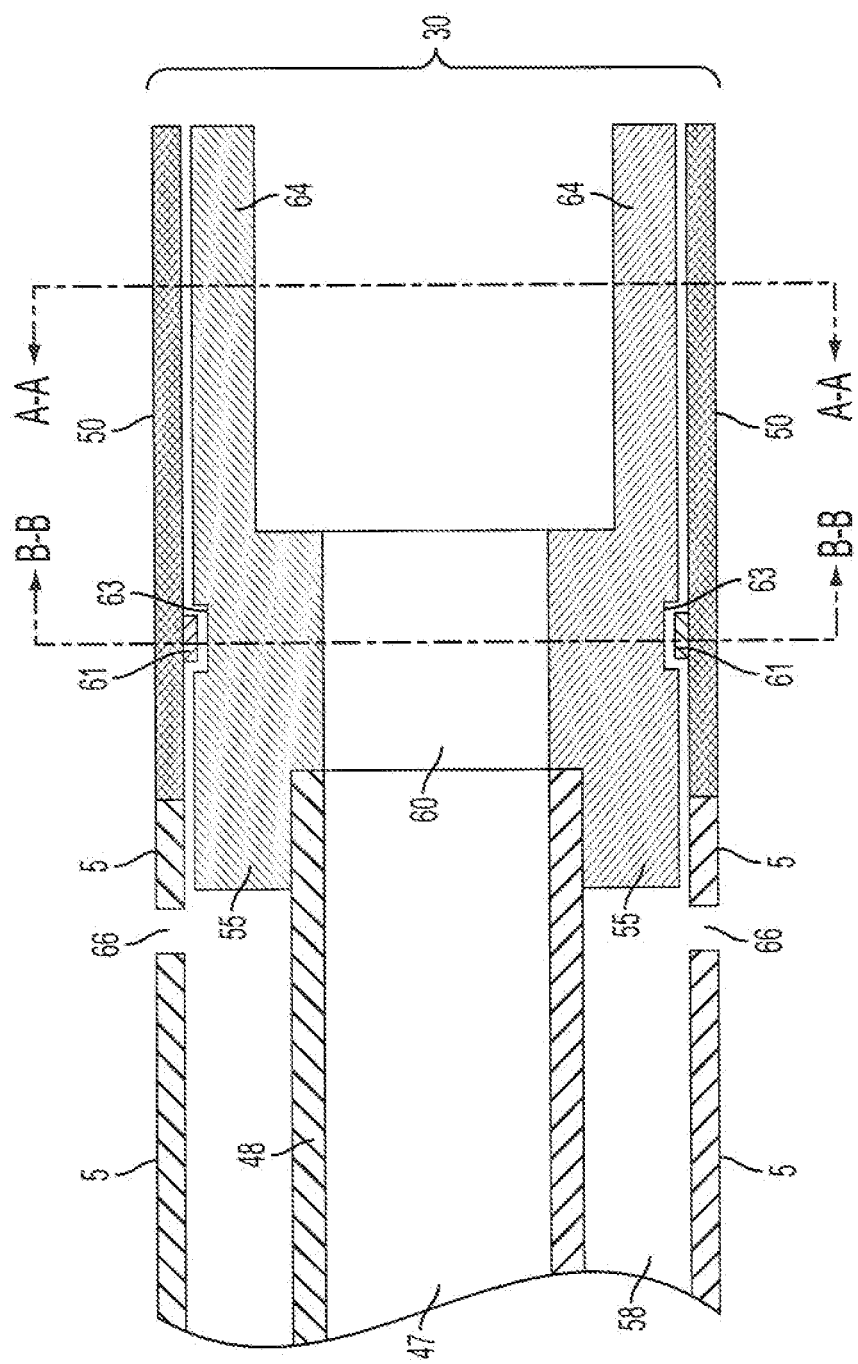
FIG. 4A is a partial, cross-sectional view of the distal portion the embodiment of FIG. 3.

FIGS. 3-4C illustrate yet another aspect of the invention. The clot removal device 1 is similar as describe above, however in this embodiment the maceration element 30 is comprised of a rotating member 64. An advantage of the macerator element 30 depicted in this embodiment, and similarly depicted in embodiments shown in FIGS. 12A-13C, is the rotating member 64 is capable of rotating at high speeds and when used in combination with aspiration or vacuum a vortex is created to aid in removal of material from vessel, as described in more detail below. The macerator element 30 of this embodiment consists of tubular extension 50 securely attached to the distal end of the outer shaft 5 and a rotating member 64 attached to the distal end of a drive shaft 48, as seen in FIG. 4A. Tubular extension 50 may be attached to the outer shaft 5 by conventional techniques such as, but not limited to, welding, adhesive bonding or step attachment and adhesive bonding, to the outer shaft 5. Tubular extension 50 includes a either a single slot 52 or a plurality of slots 52 or cut-outs. The slots 52 may be formed in a distal end 54 of the tubular extension 50.

As shown in FIG. 4A, a longitudinal drive shaft 48 may be coaxially disposed within outer shaft 5 and extends therethrough for attachment to a motor at proximal end (not shown). Near the distal end of the outer shaft 5 may be aspiration holes 66. The aspiration holes 66 may be created by drilling a hole through outer shaft 5, proximal end of tubular shaft 50, or both. A suction or vacuum apparatus (not shown) may be attached at proximal end of outer shaft 5 so when suction is applied this forces fluid and material to travel from inside vessel lumen through the aspiration holes 66 into aspiration area 58 for removal.

Figure 4B:
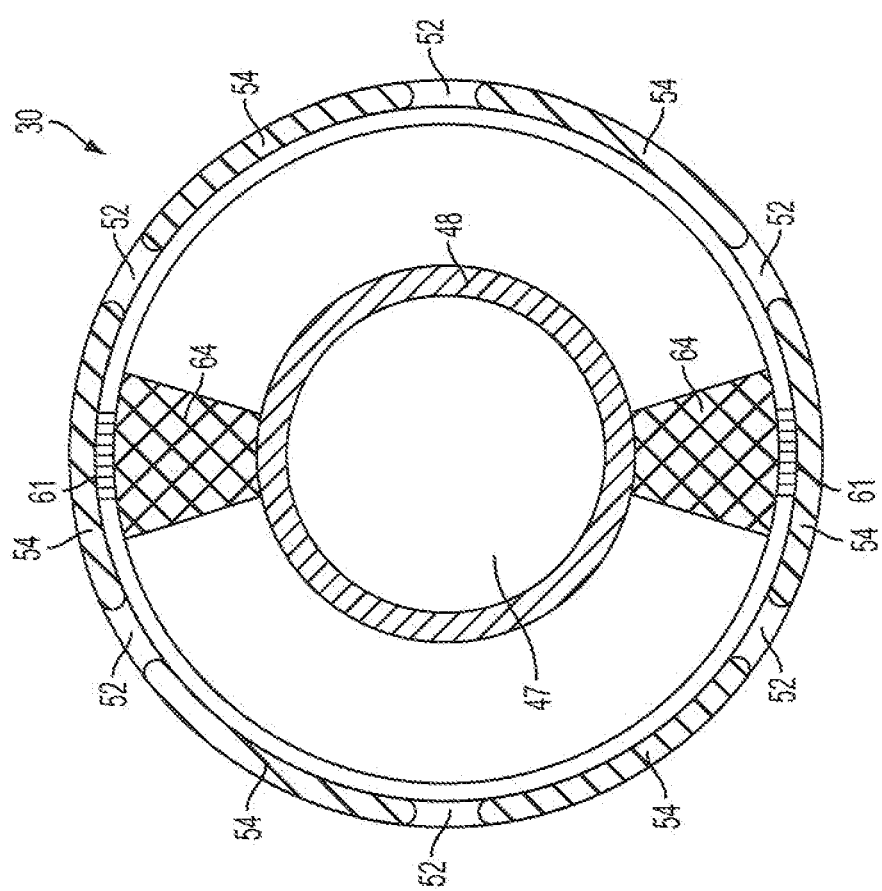
FIG. 4B illustrates a cross-sectional view of the device taken along lines A-A of FIG. 4A.
Figure 5:
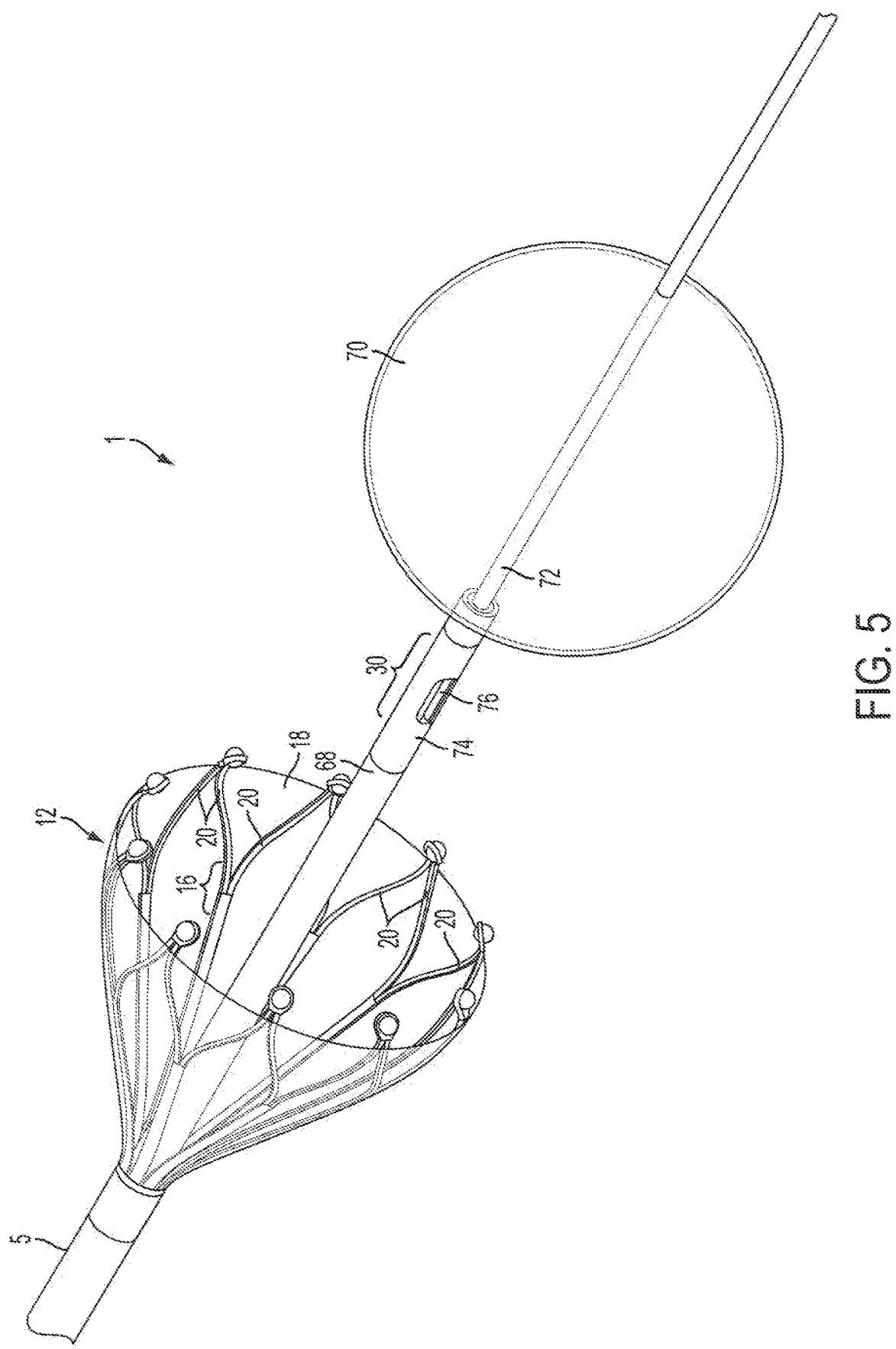
FIG. 5 is a partial, isometric view illustrating another embodiment of the expandable centering element and shearing rotating macerator element, and the device being used in combination with an embolic protection device in the form of an inflatable balloon.

The rotating member 64 may be made of PEEK, plastic, metal such as nitinol or stainless steel, or any other suitable material. The rotating member 64 may freely spin or rotate along the longitudinal axis within the distal ends 54 of tubular extension 50, as seen in FIG. 4B. A hole may be created in the distal end 55 of the rotating member 64. The size of this hole may be slightly larger than the outer diameter of the distal end 60 of the drive shaft 48 so that the distal end 60 of the drive shaft 48 may be securely inserted and fastened to the rotating member 64 via a press fit or interference fit. Alternatively, the rotating member 64 may be attached by conventional techniques such as, but not limited to, press fit, interference fit, welding, adhesive bonding or step attachment and adhesive bonding, to the distal end 60 of the drive shaft 48.

To prevent the rotating member 64 from unwanted shifting or unintended advancement inside the inner tube 5 a bulge, protuberance, extension, or bump 61 and groove 63 system may be used, as seen in FIG. 4C. The bump 61 may be an inward extension of the tubular extension 50 or an additional element connected to the inner wall of tubular extension 50. The bump 61 is sized to fit within a corresponding groove 63, notch or cut-out of the rotating member 64. Such a system will allow the rotating member 64 to freely spin and rotate within the tubular extension 50 while simultaneously preventing rotating member 64 from unintended shifting proximally or distally along the longitudinal axis.

The drive shaft 48 is rotated by activation of a motor. Conceivably, the drive shaft 48 may be capable of clockwise and/or counter-clockwise movement. Because the rotating member 64 is securely attached to drive shaft 48 both elements will rotate at the same speed. The drive shaft 48 and rotating member 64 of this embodiment may rotate up to 200,000 RPMs (rotations per minute). Rotation of the rotating member 64 within the tubular extension 50 combined with aspiration or vacuum through aspiration holes 66 may create a vortex within the vessel lumen. The vortex is created by the spinning, flowing, and swirling of turbulent fluid around the centrally located macerator element 30, such as the high speed rotation of rotating member 64. The vortex creates a force within vessel lumen that aids in pulling and detaching the clot away from the vessel wall. For example, a vortex may be created within vessel lumen and aid removal of clot material when the drive shaft 48 and rotating member 64 are rotated at speeds ranging from 10,000 rpms-80,000 rpms. In addition to creating a vortex, the rotating member 64 may be advanced towards the clot so the rotating member 64 physically cut, chop, shear, and macerate the thrombus. The combination of a dissolving clot material with the creation of a vortex and the mechanical breakdown of the clot material by the rotation of the rotating member 64 result in breaking the clot into significantly small particles and aides in drawing the macerated material into the aspiration area 58 for removal.

Referring now to FIGS. 5-8C, yet another embodiment of the clot removal device 1 is shown. In this embodiment, the clot removal device 1 may be comprised of an outer shaft 5 having a through lumen 8, an inner shaft 68, a macerator element 30 comprising of a shearing member 80. This embodiment may also have an expandable centering element 12 as described above and be using in combination with an occlusion shaft 72 having a distal occlusion element 70. If the expandable centering element 12 is used it may be securely attached near the distal end of either the outer shaft 5 or inner shaft 68. Clot removal device 1 for this embodiment may be in the range of a 6 F to 20 F in size so as to facilitate removal of clot from both small and large vessels. The shearing member 80 may be able to rotate up to approximately 10,000 rpms.

Figure 6:
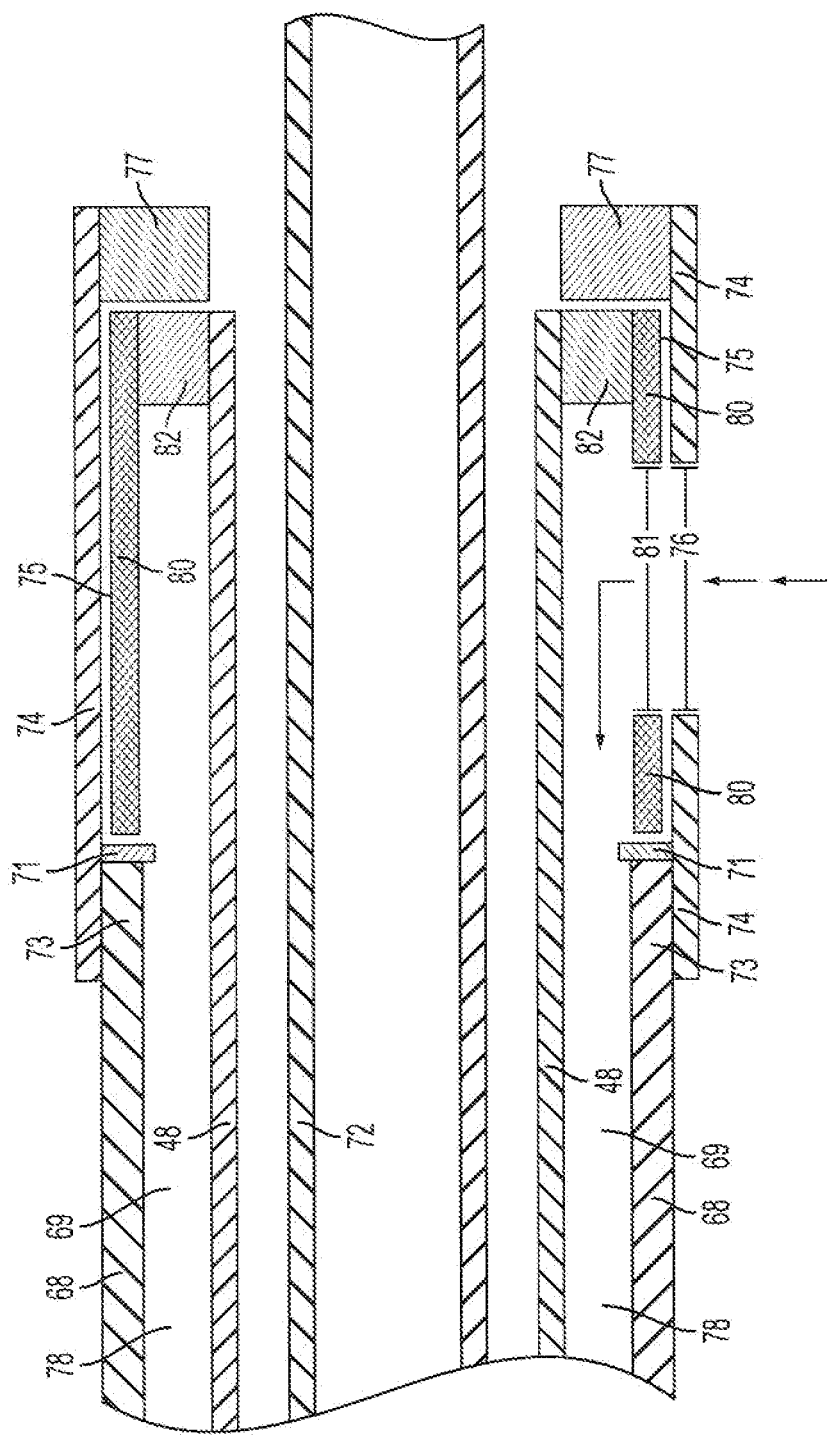
FIG. 6 is a partial, cross-sectional view of the macerator element the embodiment of FIG. 5.
Figure 7:
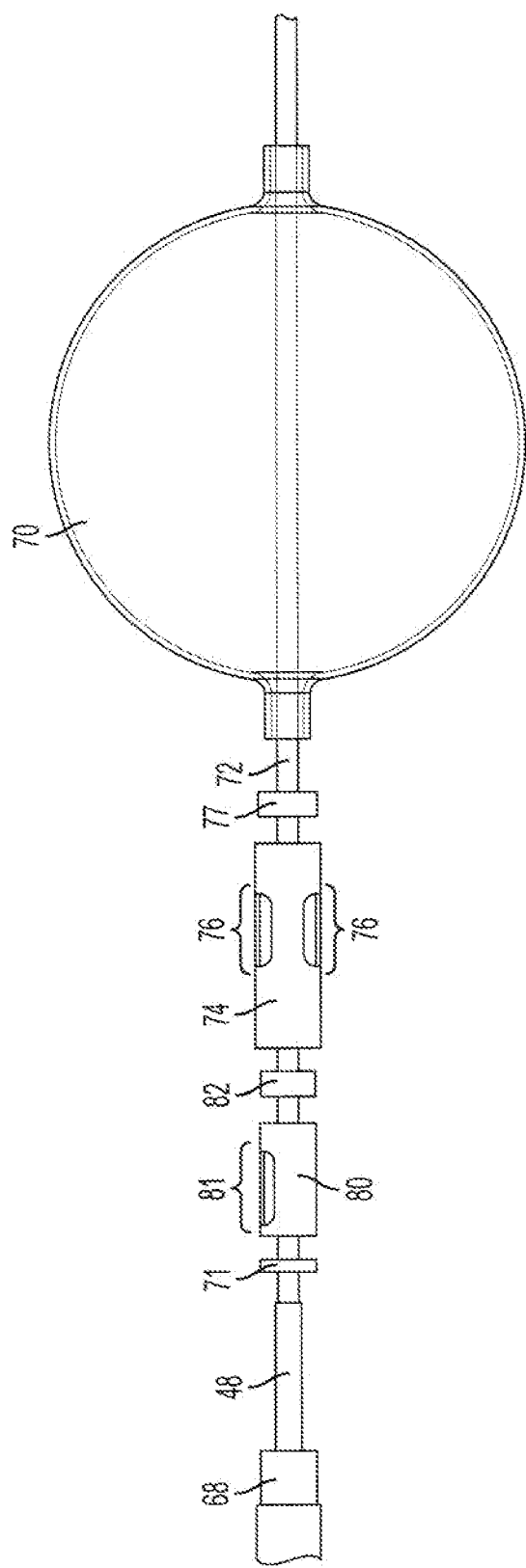
FIG. 7 depicts an assembly view of the distal portion of the device of FIG. 6.

The maceration element 30 of this embodiment consists of a stationary tubular extension 74 with a rotating shearing member 80 coaxially disposed within lumen 75 of the tubular extension 74, as seen in FIG. 6. The tubular extension 74 may be securely attached to the distal end 73 of the inner shaft 68 by conventional techniques such as, but not limited to, welding, adhesive bonding or step attachment and adhesive bonding. Tubular extension 74 includes either a single cut out 76 or a plurality of cut-outs formed by removing part of the sidewall of the tubular extension 74. The inner shaft 68 may be coaxially disposed within lumen 8 of an outer shaft 5 and extend along the entire length thereof to the proximal end (not shown) of the outer shaft 5. The inner shaft 68 may be moved independently of, or free from constraint, the outer shaft 5 so as to advance and/or retract the macerator element 30 while holding outer shaft 5 stationary. Alternatively, in another embodiment it is conceivable that inner shaft 68 is fixed relative to the outer shaft 5 so that the inner shaft 68 and outer shaft 5 move in unison.

A drive shaft 48 may be coaxially disposed within lumen 69 of the inner shaft 68 and extend therethrough to form an aspiration area 78 within the lumen 69 of the inner shaft 68. The shearing portion 80 may be coaxially disposed within the lumen 75 of the tubular extension 74 and securely attached to the distal end of the drive shaft 48 via an attachment member 82. The attachment member 82 may be secured to the distal end of the drive shaft 48 by conventional techniques such as, but not limited to, welding, adhesive bonding or step attachment and adhesive bonding. The shearing member 80 may be a tubular shape with a single cut-out 81.

A proximal collar 71 is used to prevent shearing member 80 from unwanted or unintended movement within lumen 69 of inner shaft 68. The proximal collar 71 may be either a bulge, protuberance, or extension of the inner wall of the tubular extension 74 or an additional element. Proximal collar 71 may be securely attached to the distal end of the inner shaft 68 or the inner wall of tubular extension 74. A distal collar 77 may be used to prevent the shearing member 80 from unwanted or unintended forward movement. The distal collar 77 may be either a bulge, protuberance, or extension of the inner wall of the tubular extension 74 or an additional element. The attachment member 82, proximal collar 71 and distal collar 77 may be made from metal or plastic and is secured by conventional techniques such as, but not limited to, welding, adhesive bonding or step attachment and adhesive bonding.

An external vacuum syringe or pump (not shown) may be attached to the clot removal device 1. The dislodged and broken-down clot material is aspirated by first entering through the cut outs 76 of the tubular extension 74, through the cut outs 81 of the shearing member 80, and finally enters the lumen 69 of the inner shaft 68 for removal from the body, as shown by arrows in FIG. 6.

Figure 8A:
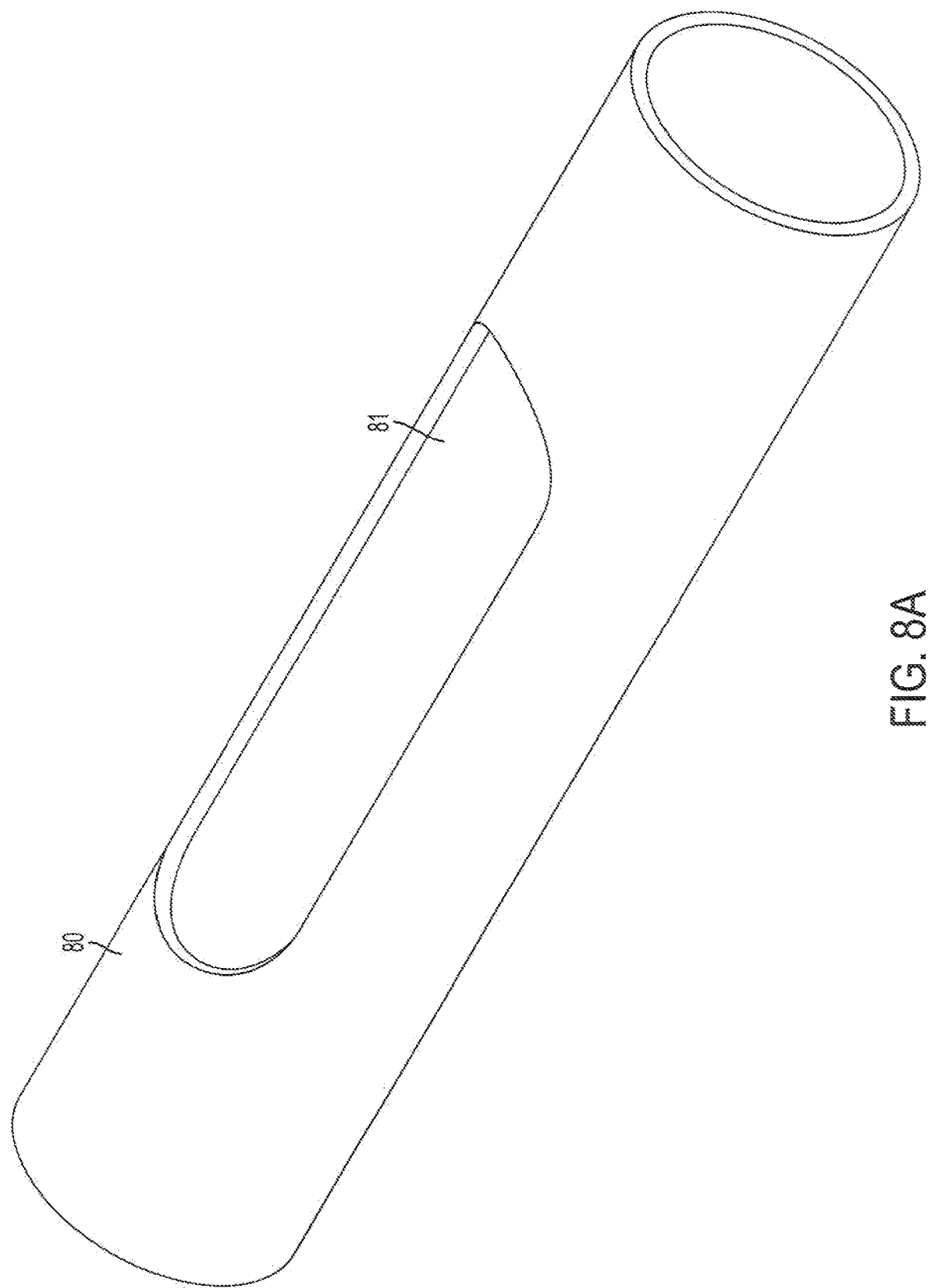
FIG. 8A is an isometric view of a rotatable shearing member.
Figure 8B:
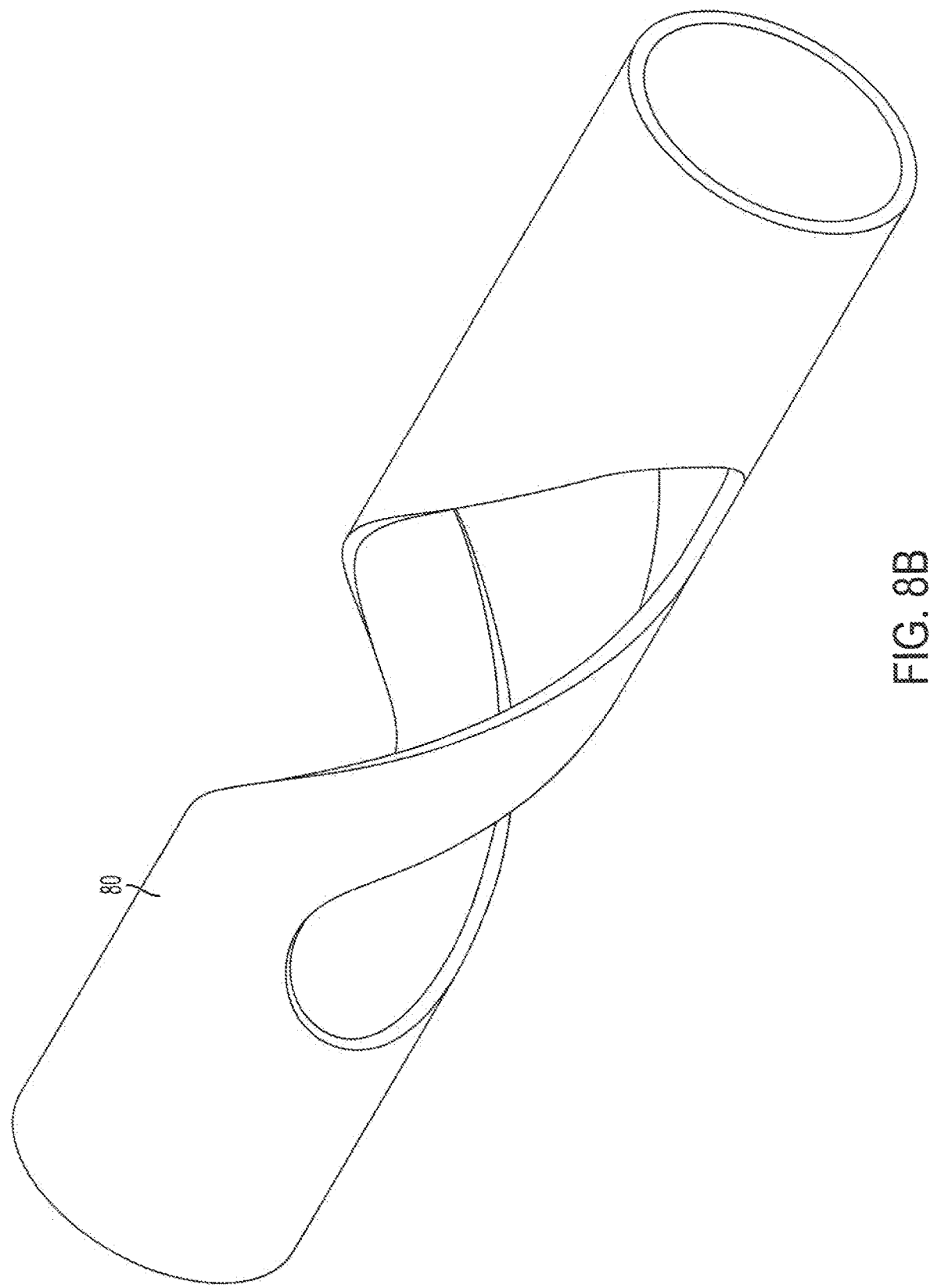
FIG. 8B is an isometric view of another embodiment of a rotatable shearing member.
Figure 8C:
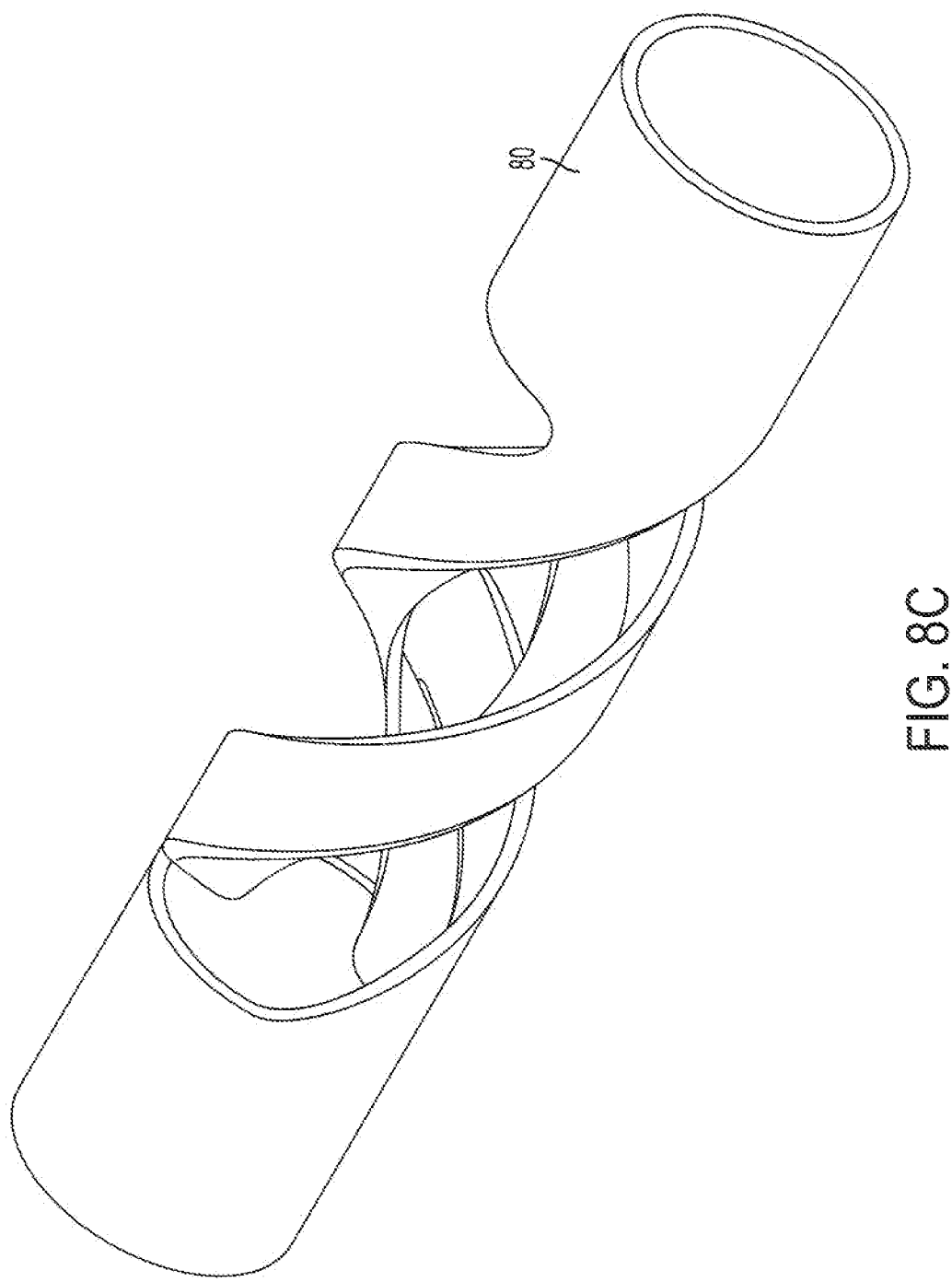
FIG. 8C is an isometric view of another embodiment of a rotatable shearing member.

The different embodiments of shearing portion 80 are seen in FIGS. 8A-8C. As seen in FIG. 8A the shearing member 80 may be a tubular shape with a single cut-out 81. Additionally, as seen in FIG. 8B-8C, the shearing member 80 may have multiple arrangements.

This embodiment may also comprise a distal occlusion element 70. Advantages of using distal occlusion element 70 include aiding in the removal of clot material and/or prevent unintended traveling or migration of dislodged clot material. The distal occlusion element 70 may comprise of either a compliant or non-compliant inflatable balloon, an embolic protection filter, an expandable wire filter, or other devices capable of expanding within vessel lumen.

The occlusion element 70 may be attached to an occlusion shaft 72 that is independent and freely movable within lumen 69 of inner shaft 68. Alternatively, occlusion shaft 72 may be securely attached to the distal end of the inner shaft 68 and move in unison together. The distal most end of the occlusion shaft 72 may comprise either a stiff end or a floppy tip end as known in the art.

Figure 10:
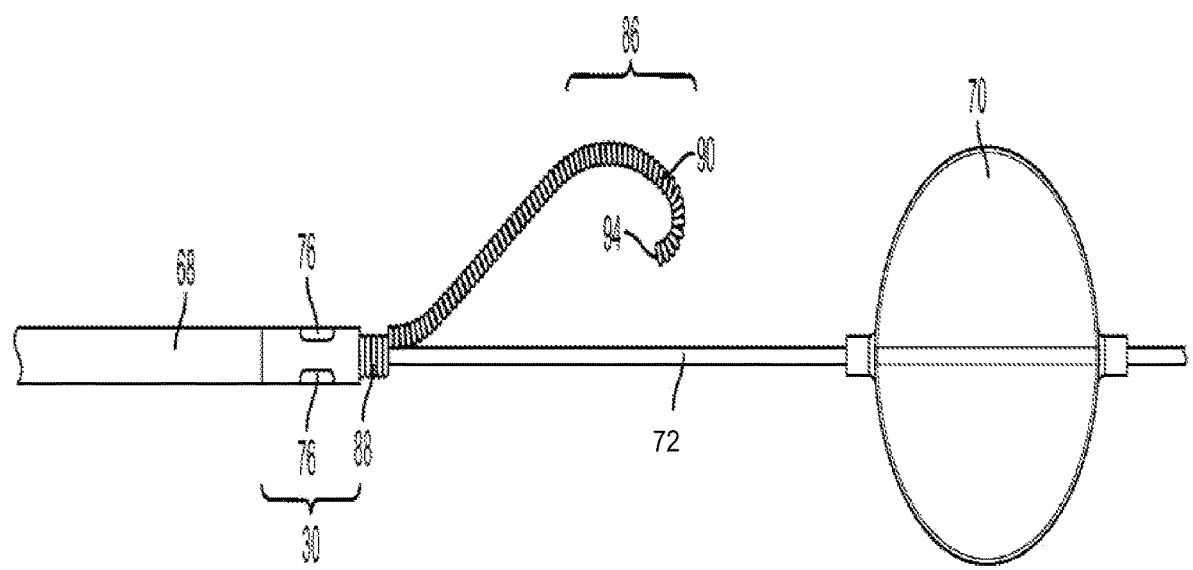
FIG. 10 is a partial side wide of a shearing macerator assembly with a rotating wire and a distal embolic protection element in the form of a balloon.

As seen in FIGS. 9-10, yet another embodiment of the device is shown. In this embodiment the clot removing device 1 is similar to what has been described and shown above but further includes a rotating wire 86 element. The rotating wire 86 element may be attached near the distal end of the drive shaft 48. An advantage of this embodiment is that as the wire 86 rotates, either clockwise or counterclockwise, it aids in breaking up and mechanically disrupting the material into smaller pieces. The rotating wire element 86 comprises a core 88 and an outer coil 90. The rotating wire 86 is coaxially attached to the device by securing the core 88 to the drive shaft 48 abutting the distal collar member 82. By securing the wire 86 to the drive shaft 48 the wire 86 will rotate at the same speed as the drive shaft 49 and shearing member 80.

The core 88 may be a solid piece of metal, such as stainless steel or nitinol, or plastic and coaxially or otherwise surrounded by an outer coil 90. The core 88 may be a single piece that has been laser cut, stamped, coiled, or compressed to form a predetermined shape. The outer coil 90 may be a solid piece of metal, such as stainless steel or nitinol, or plastic and securely attached to the core 88 via any known method of adhesion, such as welding, adhesives, or other securement means. An advantage of using an outer coil 90 to surround the core 88 is so the rotating wire 86 may have a "floppy tip" design, as known in the art, which aids in preventing damaging the vessel wall during rotation.

The wire 86 may comprise of many different shapes and size, including a straight design, coil, helix shape, or even circular. The distal occlusion shaft 72 may be coaxially disposed within the lumen of the drive shaft 48 therefore extending beyond the wire 86. The distal end 94 of the wire 86 may be independent and freely movable relative to the occlusion shaft 72 or alternatively the distal end 94 may be securely attached (not shown) to the occlusion shaft 72.

As seen in FIGS. 11A-13 yet another embodiment of the clot removal device 1 is shown. This embodiment of the clot removal device 1 is similar as to what was described above in FIG. 3-FIG. 4C, however in this embodiment the expandable member 12 element has been replaced with an inverted expandable centering element 96. An advantage of an expandable centering element 96 after it has become inverted or expanded, as described in more detail below, the apex of the centering element 96 may be parallel or in front of the distal most end of the macerator element 30. Another benefit of this embodiment is that when the device is used in tortuous anatomy the expandable centering element 96 will be less likely to catch, snag, engage, or rupture the vessel walls, and in turn promote advancement of the clot removal device 1. Yet another advantage of this embodiment is less chance for unwanted advancement or "snow plowing" of the clot material away from the macerator element 30. Clot removal device 1 for this embodiment may be in the range of a 6 F to 20 F in size so as to facilitate removal of clot from both small and large vessels.

Figure 11A:
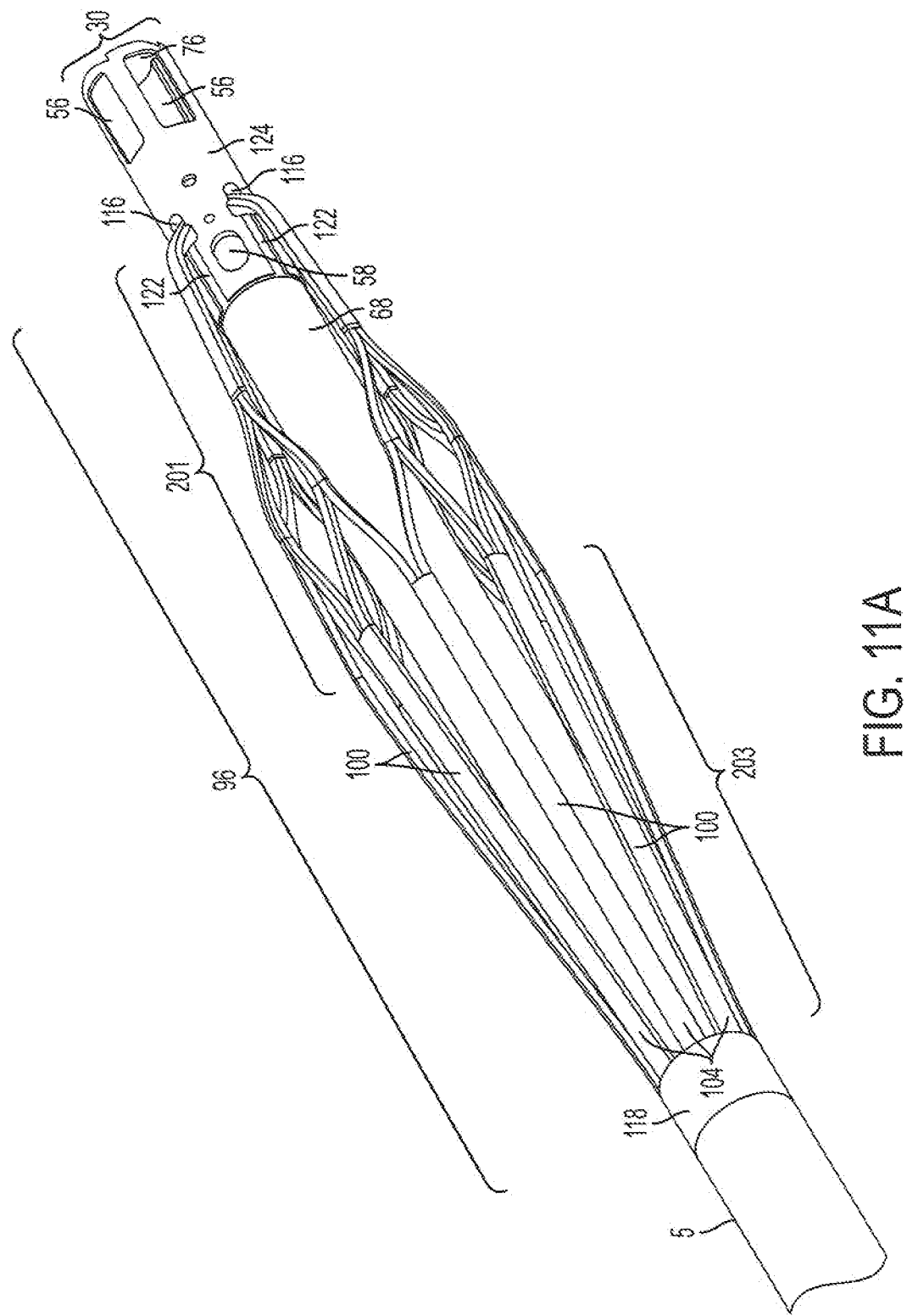
FIG. 11A depicts a partial, isometric view of the distal portion of the device illustrating a manually expandable cage in a retracted, undeployed position.
Figure 11B:
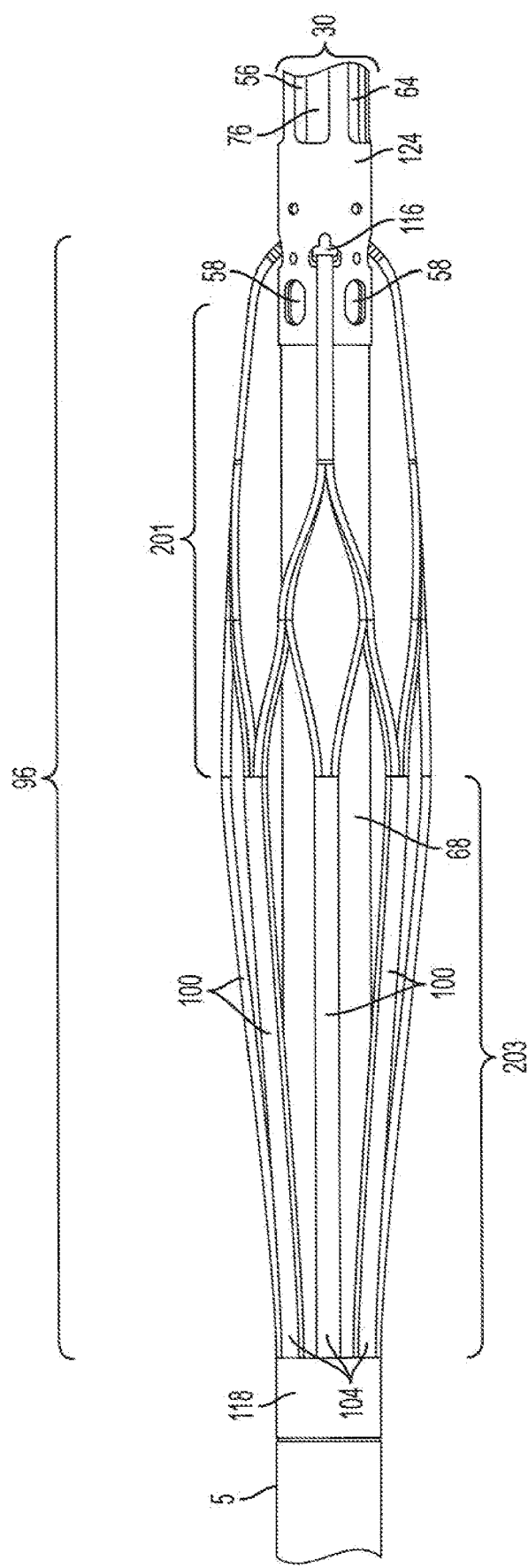
FIG. 11B is a partial, plan view of the distal portion of the device depicting the manually expandable cage in a retracted, undeployed position.

The expandable centering element 96 is attached to the clot removal device 1 via an secured attachment 116. The secured attachment 116 provides the user the ability to manually expand or invert the expandable centering element 96. For this embodiment the outer shaft 5 coaxially surrounds and is freely moveable relative to the inner shaft 68. An advantage of this embodiment is that during placement of the clot removal device 1 the expandable centering element 96 may be collapsed, pulled taut, or "non-inverted", as seen in FIG. 11A-11C. A non-inverted or collapsed expandable centering element 96 may facilitate advancement, placement, adjustment during use, or removal of the device 1. When expandable centering element 96 is in the non-inverted or collapsed position the proximal bulge 125 of the secured attachment 116 is pulled taut and toward the proximal end of the device, as shown in FIG. 11C. Conversely, when the expandable centering element 96 is in the inverted or expanded position the proximal bulge 125 of the secured attachment 116 is pushed toward the distal end of the device, as seen in FIG. 12B.

Figure 12A:
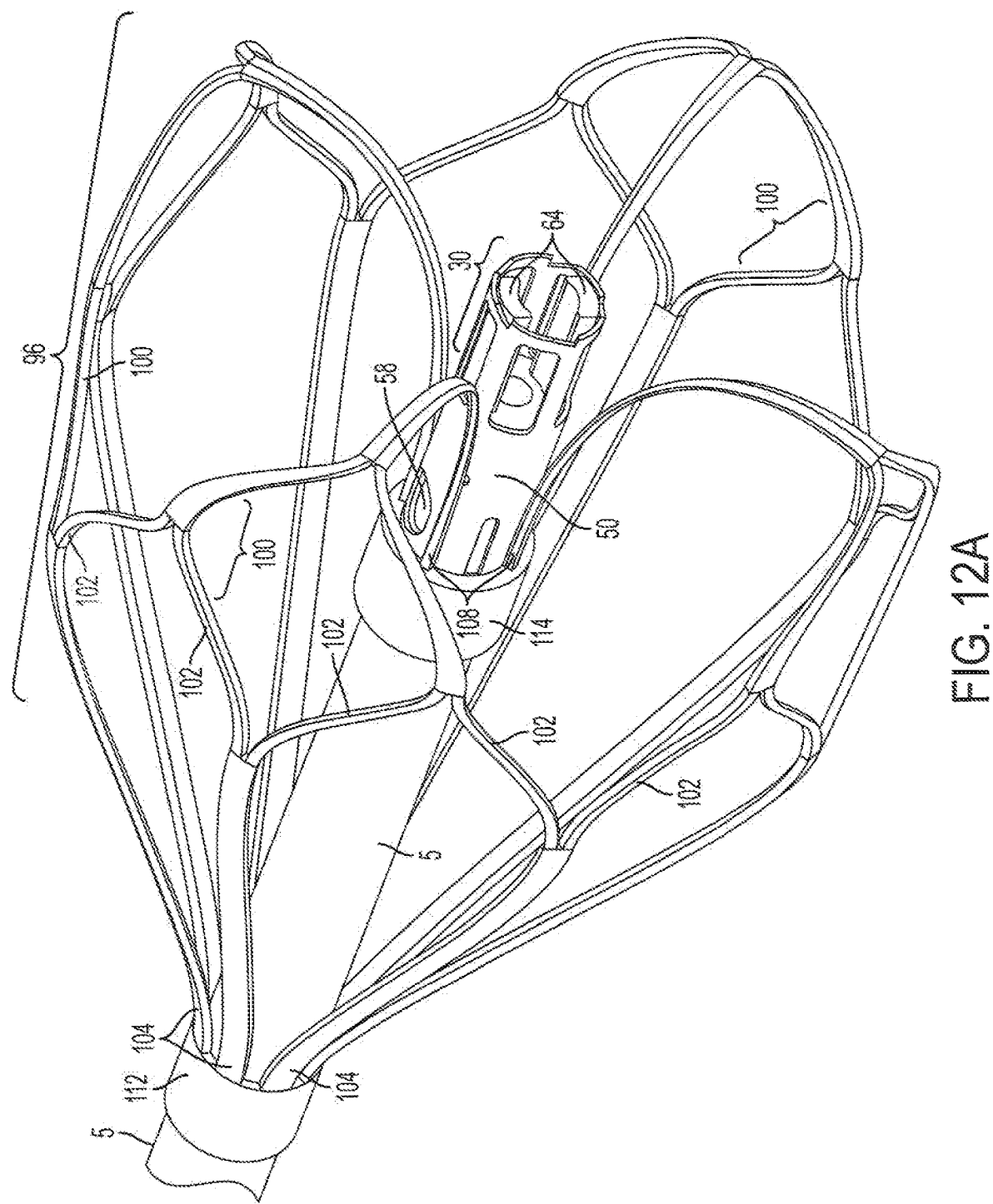
FIG. 12A is a partial, isometric view of the distal portion of the device illustrating an expandable cage in a deployed position.
Figure 12B:
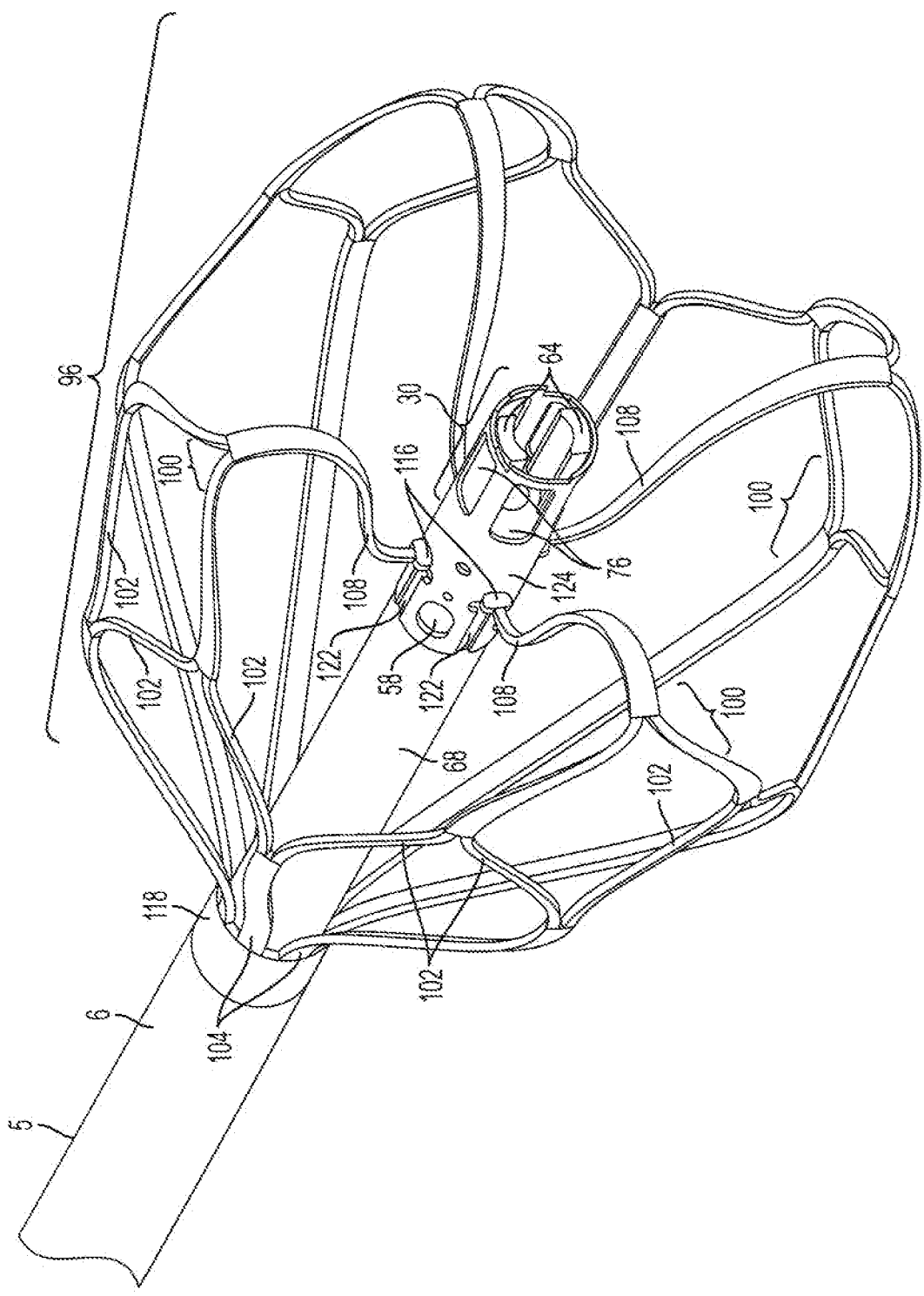
FIG. 12B is a partial, isometric view of the distal portion of the device illustrating a manually expandable cage in a deployed position.
Figure 12C:
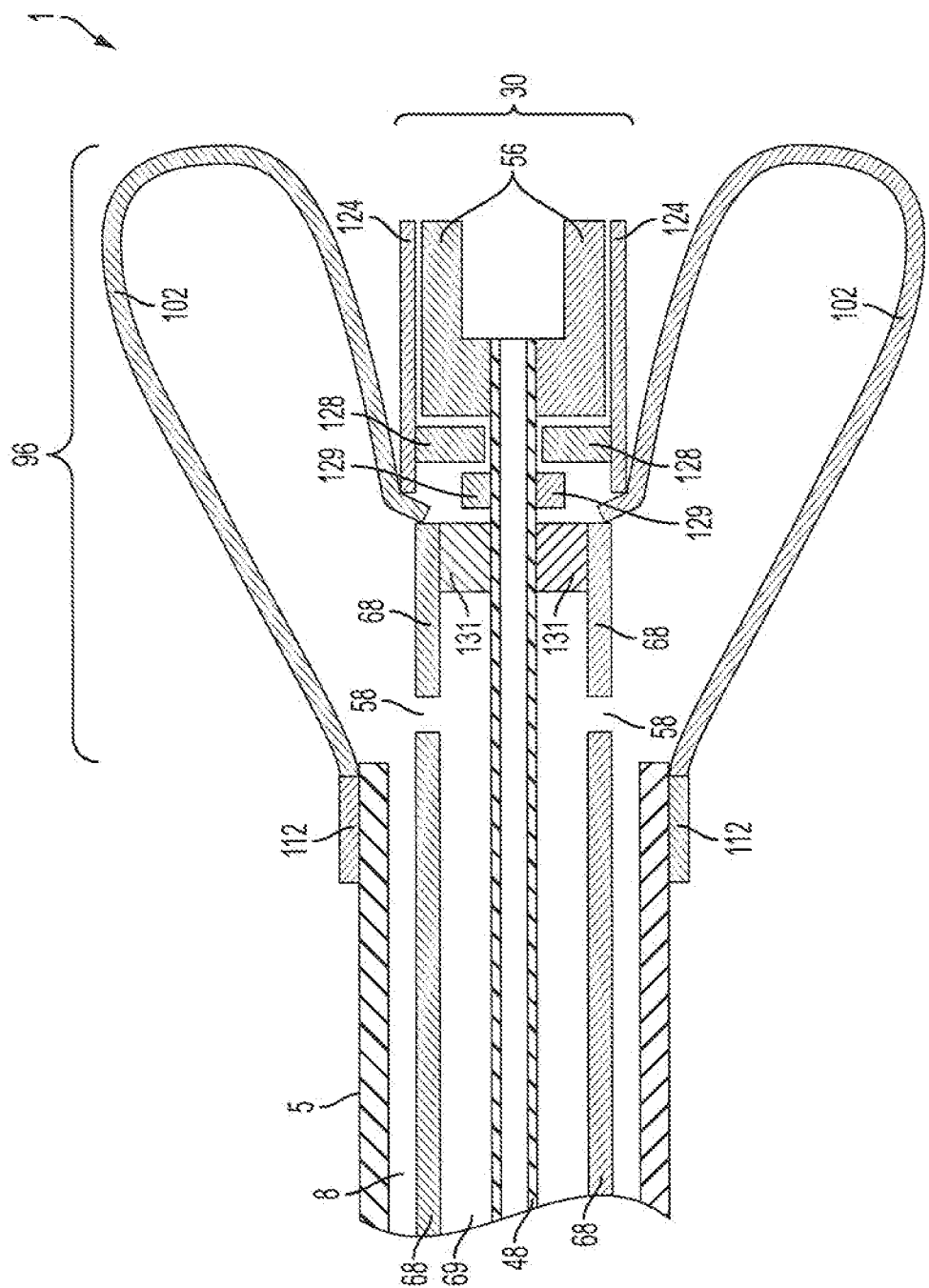
FIG. 12C illustrates an enlarged, cross-sectional view of the manually expandable cage section in a partially deployed position.

The user may manually "invert" or expand the centering element 96 so the apex of the expandable centering element 96 may be parallel or slightly proximal of the macerator element 30, as seen in FIG. 12B-12C. The expandable centering element 96 may be inverted or expanded by holding the outer shaft 5 stationary and retracting the inner shaft 68 or holding the inner shaft 68 stationary and advancing outer shaft 5.

In this embodiment the proximate end 104 of each converging wire member 102 may be attached to the distal end 6 outer shaft 5 via an outer shaft collar 118. The wire members may be made from a shape memory material such as nitinol, or other material such as stainless steel or plastic. The distal ends 108 of the wire members 102 may be securely attached to the distal end of the inner shaft 68 via a secured attachment 116. The secured attachment 116 allows for distal and proximal movement of the distal ends 108 of the wire members 102 while securely coupling the distal bulge 127 of each wire member 102 within the empty space abutting the distal end of the inner shaft 68.

The macerator element 30 of this embodiment comprises of an outer tubular extension 124 having either a single cut out 76 or slot or a plurality of cut-outs or slots and rotating finger elements 56. Extending coaxially along the lumen 69 of inner shaft 68 is the drive shaft 48 with its distal end securely attached to rotating finger elements 56 via a press fit, or interference fit. Alternatively, other macerator elements described above may be used in combination with the inverted expandable centering element 96, such as the rotating member 64, shearing member 80, auger 32, or rotating wire 86.

To prevent the drive shaft 48 from unwanted forward or backward movement a proximal stopper 131 and distal stopper 128 are used in combination with crimp tube 129. The proximal stopper 131 abuts the distal most end 123 of the inner shaft 68 and is securely attached to tubular extension 125 via conventional techniques such as, but not limited to, welding or adhesive bonding. The proximal stopper 131 may be an additional element attached to inner wall of inner shaft 68 or a bulge, protuberance, or extension of the inner wall of the inner shaft 68. The crimp tube 129 may be crimped or securely attached to the drive shaft 48 at a position between the proximal stopper 131 and distal stopper 128. The distal stopper 128 may be attached to the tubular extension 124 via conventional techniques such as, but not limited to, welding or adhesive bonding, at a selected distance distal from the end of the crimp tube 129. The proximal stopper 131 may be an additional element attached to inner wall of the tubular extension 124 or a bulge, protuberance, or extension of the inner wall of the tubular extension 124. The proximal stopper 131, distal stopper 128 and crimp tube 129 may be made from hypo-tubing, metal, plastic, or other suitable material. In use, the crimp tube 129 is enclosed between the proximal stopper 131 and distal stopper 128 in order to prevent the drive shaft 48 from unintentionally advancing or retracting within lumen 69 of inner shaft 68.

The tubular extension 124 is securely attached to inner shaft 68 via conventional techniques such as, but not limited to, welding or adhesive bonding. An aspiration area 58 is created by drilling a hole through tubular extension 124 and inner shaft 68 near the distal end of the macerator shaft 68. This aspiration area 58 creates an open channel or hole from the lumen 69 of the inner shaft 68 through the body of the shaft 68 and tubular extension 124. In use, the user may elect to apply suction or vacuum through the lumen 69 of the inner shaft 68 which may create a vortex within the vessel and aspirate clot material through aspiration area 58.

Figure 13:
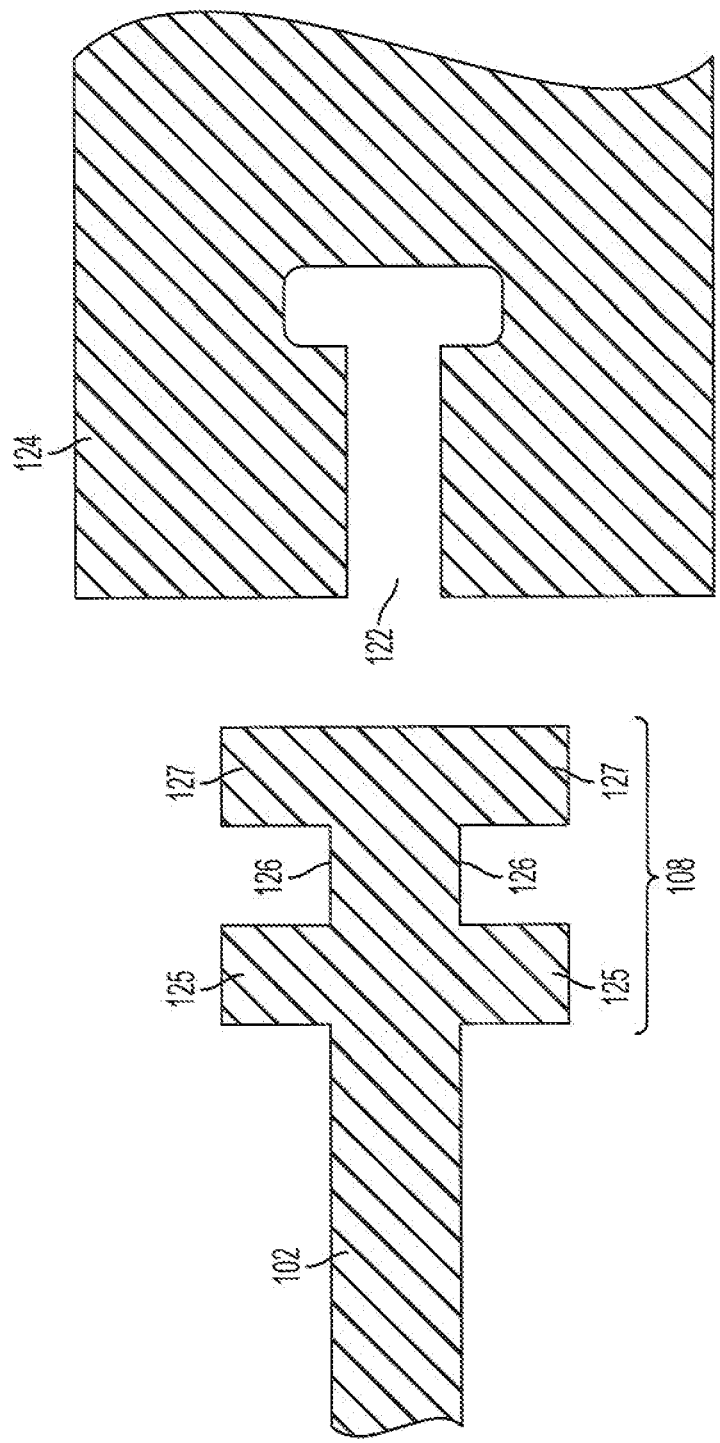
FIG. 13 is a further enlarged, cross-sectional view of the manually expandable cage section illustrating the position of the distal ends of the wire legs of the cage.

As seen in FIG. 13 distal ends 108 of the wire members 102 may have a proximal bulge 125, a groove or notch 126, and a distal bulge 127, creating an "H" shape at the distal end 108. The tubular extension 124 may comprise slits 122 along the proximal end. The number of slits 122 correspond with the number of distal ends 108 requiring securement via the secured attachment 116. Prior to attaching tubular extension 124 to inner shaft 68 the notch 126 of the distal end 108 of the wire member 102 is slid into the slits 122 on the proximal end of the tubular extension 124. The tubular extension 124 is then securely attached to the distal end of the inner shaft 68 by conventional techniques such as, but not limited to, welding or adhesive bonding. After tubular extension 124 is securely attached to inner shaft 68 the secure attachment 116 is created because the distal bulge 127 will be securely enclosed within the empty space abutting the distal end of the inner shaft 68 while the proximal bulge 125 will be located and freely movable atop the tubular extension 124. The notch 126 will be enclosed between the distal end of the inner shaft 68 and the slit 122 of the tubular extension 124.

As seen in FIG. 12A, yet another embodiment of the inverted expandable centering element 96 is shown. The proximal end 104 of each wire member 102 may be securely attached to the outer shaft 5 at a proximal collar 112. The distal ends 108 of each wire member 102 are securely attached to the outer shaft 5 at a distal collar 114. In this embodiment, the distance between proximal collar 112 and distal collar 114 is fixed. Clot removal device 1 may be in the range of a 6 F to 20 F in size so as to facilitate removal of clot from both small and large vessels. The proximate collar 112 is securely attached to the outer shaft 5 via conventional techniques such as, but not limited to, adhesive bonding. The distal ends 108 of the wire members 102 may be inverted, meaning bent inward towards the shaft 5 and then back towards the proximal collar 114, and securely attached to the outer shaft at a distal collar 114. The distal collar 114 may be securely attached to the inner shaft 68 via conventional techniques such as, but not limited to, adhesive bonding. Alternatively, if no inner shaft 68 is used then the distal collar 114 may be securely attached to distal end of the outer shaft 5.

Other attachment configurations are also possible, such as attaching the distal ends 108 of the wire members 102 at the same position along the distal end 6 of the outer shaft 5. Further, the wire members 102 of the expandable centering element 96 may be made of a number of different materials capable of expanding to a pre-determined shape, such as stainless steel or nitinol.

In use the clot removal device 1 may be introduced into the target vessel or other anatomical site using minimally invasive access techniques known in the art. If a distal occlusion element 70 is being used in combination with the device 1 the user may elect to place the occlusion element 70 using known techniques in the art prior to insertion of the device 1. Once the distal occlusion element 70 has been properly inserted and placed beyond the clot, the device 1 may be back-loaded over a pre-placed guidewire. Alternatively, the user may elect to insert the device 1 at the target area and then insert the distal occlusion element 70 into through lumen of the drive shaft 48.

During insertion the expandable member 12 or expandable centering element 96 may be collapsed within a procedure sheath to aid in advancement and placement of the device 1. The clot removal device 1 may be advanced into position adjacent the clot. The procedure sheath may be retracted, or the device 1 may be advanced holding the sheath stationary, allowing for automatic deployment of the expandable member 12 or expandable centering element 96, or manual expansion of the expandable member 12 or expandable centering element 96 may be done by the user if required.

Placement and expansion of the expandable member 12 or inverted expandable centering element 96 centers the macerator element 30 of the clot removal device 1 within the vessel lumen. An advantage of centering the clot removal device 1 within the vessel lumen is that the macerator element 30 will be less likely to engage, damage, rupture, or puncture the vessel wall. Another advantage of centering the macerator element 30 is the decrease in likelihood of clogging or disrupting the movement of the macerator element 30. Once fully expanded, the expandable member 12 or expandable centering element 96 may either be held stationary during use or may be advanced toward the clot mass to aid in the removal of clot material.

After the macerator element 30 and distal occlusion element 70 are in place the drive shaft 48 may be activated. The speed and rotation of the drive shaft 48 will depend on the type of macerator element 30 being used and the requirements of the treatment. Activation of the drive shaft 48 may cause either clockwise or counter-clockwise rotation of macerator element 30. Upon activation of the drive shaft 48 and rotation of the macerator element 30 the material for removal, such as a clot, will start to macerate, break down, separate, chop, or remove clot from the vessel.

Although the current design anticipates disruption of the clot material without the use of a lysing agent, a practitioner may optionally consider the use of a lysing agent in combination with the use of the device 1 at any time during the procedure. The device and method for introducing the lysing agent may be at the discretion of the practitioner. However, if a practitioner elects to use the clot removal device 1 in combination with a lysing agent or other drug this fluid may be introduced into the through lumen 8 of the outer shaft 5 or through the lumen 68 of the inner shaft 68 and injected into the vessel.

Once the clot has been significantly broken down into smaller pieces and removed through aspiration or vacuum, the distal occlusion element 70 may be retracted toward the expandable member 12 or expandable centering element 96 to aid in the capture of any loose clot fragments and disengagement of any clot mass remaining attached to the vessel wall. The essentially smaller clot particles and the liquefied clot material disposed within the lumen 69 of the inner shaft 68 may be fully removed from the vessel to a location external of the clot removal device 1.

Upon completion of the procedure, the distal occlusion element 70 and macerator element 30 may be retracted within the through lumen 8 of the outer shaft 5, or optionally through a procedure sheath if no outer sheath 5 is being used. The expandable member 12 or expandable centering element 96 may then be retracted within the procedure sheath thereby removing any potentially remaining clot particles may be captured in the expandable member 12 or expandable centering element 96. The clot removal device 1 may then be withdrawn from the patient. This method contemplates clot disruption and removal with minimum risk of injury to the vessel.

The invention claimed is:

1. A device comprising:
an outer shaft comprising an outer shaft distal end;
an inner shaft comprising an inner shaft lumen and an inner shaft distal end;
a distal leading end attached to the inner shaft distal end;
a macerator element comprising a rotating member and a rotating member lumen;
wherein the inner shaft coaxially extends through the rotating member lumen such that the inner shaft distal end extends a certain distance distally beyond a distal most end of the macerator element; and
an expandable member comprising an expandable member proximal end and an expandable member distal end; wherein the expandable member proximal end is attached to the outer shaft distal end; and wherein the expandable member distal end is attached to the distal leading end.

2. The device of claim 1, wherein the expandable member further comprises a wire frame and a non-permeable member configured to cover at least a section of the wire frame.

3. The device of claim 2, wherein the leading distal end further comprises a distal leading end proximal portion; wherein the expandable member distal end is attached to the distal leading end proximal portion.

4. The device of claim 1, further comprising a drive shaft comprising a drive shaft distal end attached to the rotating member; wherein the rotating member is configured to rotate up to 100,000 rotations per minute.

5. The device of claim 1, wherein the inner shaft lumen is configured to allow the device to be coaxially placed over a medical device.

6. The device of claim 5, wherein the medical device is a guidewire.

7. The device of claim 1, wherein the inner shaft is coaxially disposed within the outer shaft.

8. The device of claim 7, wherein the inner shaft is independently moveable relative to the outer shaft.

9. The device of claim 1, wherein the distal leading end further comprises an open distal tip.

10. A device comprising:
an outer shaft comprising an outer shaft distal end;
an inner shaft comprising an inner shaft lumen and an inner shaft distal end;
a distal leading end attached to the inner shaft distal end;
a rotating member and a rotating member lumen;
wherein the inner shaft coaxially extends through the rotating member lumen such that the inner shaft distal end extends a certain distance distally beyond a distal most end of the rotating member;
a drive shaft comprising a drive shaft distal end attached to the rotating member; and
an expandable member comprising an expandable member proximal end and an expandable member distal end; wherein the expandable member proximal end is attached to the outer shaft distal end; and wherein the expandable member distal end is attached to the distal leading end.

11. The device of claim 10, further comprising a housing, a housing sidewall, and an opening in the housing sidewall; wherein the rotating member is coaxially disposed within the housing and wherein the opening in the housing sidewall is configured to be in fluid communication with an aspiration lumen.

12. The device of claim 11, wherein the drive shaft is attached to a drive mechanism.

13. The device of claim 12, wherein the inner shaft is configured to be freely moveable relative to the outer shaft.

14. The device of claim 10, wherein the expandable member comprises at least two wires.

15. A device comprising:
an outer shaft comprising an outer shaft distal end;
an inner shaft comprising an inner shaft distal end;
a distal leading end attached to the inner shaft distal end;
a rotating macerator and a rotating macerator lumen;
wherein the inner shaft coaxially extends through the rotating macerator lumen such that the inner shaft distal end extends a certain distance distally beyond a distal most end of the rotating macerator; and
an expandable member comprising an expandable member proximal end, an expandable member distal end; wherein the expandable member proximal end is attached to the outer shaft distal end; and wherein the expandable member distal end is attached to the distal leading end.

16. The device of claim 15, wherein the expandable member comprises at least two wire members.

17. The device of claim 16, wherein the expandable member further comprises a cover.

18. The device of claim 16, wherein the cover comprises a permeable material.

19. The device of claim 16, wherein the distal leading end is configured to provide for an atraumatic distal end.

20. The device of claim 18, wherein the inner shaft further comprises an inner shaft lumen; wherein the distal leading end further comprises an open distal tip; and wherein the open distal tip may be configured such that the device may be placed coaxially over a proximal end of a guidewire.

\* \* \* \* \*